US008755867B2

(12) United States Patent
Inoue et al.

(10) Patent No.: US 8,755,867 B2
(45) Date of Patent: Jun. 17, 2014

(54) OPTICAL MEASUREMENT SYSTEM, PORTABLE OPTICAL MEASUREMENT DEVICE USED THEREIN, AND REHABILITATION PLANNING METHOD USING SAME

(75) Inventors: Yoshihiro Inoue, Kyoto (JP); Takashi Amita, Kyoto (JP); Satoru Kohno, Kyoto (JP); Akihiro Ishikawa, Kyoto (JP); Yoshinori Masuda, Kyoto (JP); Haruhide Udagawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/512,957

(22) PCT Filed: Dec. 1, 2009

(86) PCT No.: PCT/JP2009/070200
§ 371 (c)(1),
(2), (4) Date: May 31, 2012

(87) PCT Pub. No.: WO2011/067833
PCT Pub. Date: Jun. 9, 2011

(65) Prior Publication Data
US 2012/0238883 A1    Sep. 20, 2012

(51) Int. Cl.
*A61B 6/00*    (2006.01)

(52) U.S. Cl.
USPC .......................................................... 600/476

(58) Field of Classification Search
None
See application file for complete search history.

(56) References Cited

U.S. PATENT DOCUMENTS 7,039,454 B1    5/2006  Kaga et al.
8,277,385 B2 *  10/2012 Berka et al. .................. 600/485

2004/0077951 A1*  4/2004  Lin et al. ........................ 600/476
2004/0167381 A1*  8/2004  Lichter et al. .................. 600/300
2006/0063995 A1*  3/2006  Yodh et al. ..................... 600/323
2007/0225611 A1*  9/2007  Kumar et al. .................. 600/523
2008/0287821 A1* 11/2008  Jung et al. ...................... 600/544

FOREIGN PATENT DOCUMENTS

| JP | 2001-337033 A | 12/2001 |
|---|---|---|
| JP | 2002-143169 A | 5/2002 |
| JP | 2002-323445 A | 11/2002 |
| JP | 2006-305372 A | 11/2006 |
| JP | 2007-236963 A | 9/2007 |
| JP | 2009-45479 A | 3/2009 |
| JP | 2009-189576 A | 8/2009 |
| WO | 00/57793 A1 | 10/2000 |

OTHER PUBLICATIONS

G. S. Strangman, Factors affecting the accuracy of near-infrared spectroscopy concentration calculations for focal changes in oxygenation parameters, NeuroImage, 18 (2003) pp. 865-879.

* cited by examiner

*Primary Examiner* — Long V. Le
*Assistant Examiner* — Kevin Pontius
(74) *Attorney, Agent, or Firm* — McDermott Will & Emery LLP

(57) ABSTRACT

An optical measurement system has main and portable optical measurement devices. The main optical measurement device includes Ath first light sending devices and Bth first light receiving devices. The portable optical measurement device includes Cth second light sending devices for illuminating a subject, Dth second light receiving devices receiving light from the subject, a holder worn on a head of the subject and having through holes therein, a control unit acquiring measurement data relating to a brain activity while controlling the second light sending and receiving devices, and a communication device communicating with the main optical measurement device. (C+D)<(A+B) is satisfied. The communication device of the portable optical measurement device transmits the measurement data acquired by the control unit of the portable optical measurement device to the main optical measurement device.

7 Claims, 17 Drawing Sheets

OPTICAL MEASUREMENT SYSTEM, PORTABLE OPTICAL MEASUREMENT DEVICE USED THEREIN, AND REHABILITATION PLANNING METHOD USING SAME

CROSS REFERENCE TO PRIOR APPLICATIONS

This application is a U.S. National Phase application under 35 U.S.C. §371 of International Application No. PCT/JP2009/070200, filed on Dec. 1, 2009. The International Application was published in Japanese on Jun. 9, 2011 as WO 2011/067833 A1 under PCT Article 21(2). All of the applications are herein incorporated by reference.

TECHNICAL FIELD

The present invention relates to an optical measurement system for non-invasively measuring information inside a living thing (measurement data) using light, a portable optical measurement device used therein, and a rehabilitation planning method using the same, and in particular, a multichannel type optical measurement system having a number of light sending points for illuminating a living thing with light and a number of light receiving points for receiving light emitted from the living thing, where information inside the living thing is measured for a number of channels that are set for each combination of one light sending point and one light receiving point, a portable optical measurement device used therein, and a rehabilitation planning method using the same.

The present invention is applied to a medical device for measuring brain functions and for diagnosing circulatory disorders by measuring a chronological change in the blood flow through each portion within the brain or a change in the supply of oxygen inside a living thing, for example.

BACKGROUND

In recent years, optical imaging devices for simply and non-invasively measuring brain functions using light have been developed in order to observe the state of the brain's activity. In these optical imaging devices for measuring the brain functions, light sending probes placed on the surface of the head of a subject irradiate the brain with near-infrared rays having three different wavelengths: $\lambda_1$, $\lambda_2$ and $\lambda_3$ (780 nm, 805 nm and 830 nm, for example), and at the same time, light receiving probes placed on the surface of the head detect the intensity of the near-infrared rays (information on the amount of received light) $A(\lambda_1)$, $A(\lambda_2)$ and $A(\lambda_3)$ of the respective wavelengths $\lambda_1$, $\lambda_2$ and $\lambda_3$ emitted from the brain.

In order to find the product of the concentration of the oxyhemoglobin in the blood flow in the brain and the length of the optical path [oxyHb] and the product of the concentration of the deoxyhemoglobin and the length of the optical path [deoxyHb] from the thus-obtained information on the amounts of received light $A(\lambda_1)$, $A(\lambda_2)$ and $A(\lambda_3)$, simultaneous equations (1) to (3) are created using the modified Beer-Lambert Law, for example, and the simultaneous equations are solved (see Factors affecting the accuracy of near-infrared spectroscopy concentration calculations for focal changes in oxygenation parameters, NeuroImage 18, 865-879, 2003). Furthermore, the product of the concentration of the total amount of hemoglobin and length of the optical path ([oxyHb]+[deoxyHb]) is calculated from the product of the concentration of oxyhemoglobin and the length of the optical path [oxyHb] and the product of the concentration of deoxyhemoglobin and the length of the optical path [deoxyHb].

$$A(\lambda_1)=E_O(\lambda_1)\times[\text{oxyHb}]+E_d(\lambda_1)\times[\text{deoxyHb}] \quad (1)$$

$$A(\lambda_2)=E_O(\lambda_2)\times[\text{oxyHb}]+E_d(\lambda_2)\times[\text{deoxyHb}] \quad (2)$$

$$A(\lambda_3)=E_O(\lambda_3)\times[\text{oxyHb}]+E_d(\lambda_3)\times[\text{deoxyHb}] \quad (3)$$

Here, $E_O(\lambda_m)$ is the absorbance coefficient of oxyhemoglobin for light having a wavelength $\lambda_m$, and $E_d(\lambda_m)$ is the absorbance coefficient of deoxyhemoglobin for light having a wavelength $\lambda_m$.

Here, the relationship between the distance (channel) between a light sending probe and a light receiving probe and the measurement portion is described. FIG. 12A is a cross-sectional diagram showing the relationship between a pair of a light sending probe and a light receiving probe and the measurement portion, and FIG. 12B is a plan diagram of FIG. 12A.

A light sending probe 12 is pressed against the surface of the head of a subject at a light sending point T, and at the same time, a light receiving probe 13 is pressed against the surface of the head of the subject at a Light receiving point R. Thus, the light sending probe 12 emits light, and at the same time, light emitted from the surface of the head enters into the light receiving probe 13. At this time, light emitted from the light sending point T on the surface of the head and that has passed through a banana-shaped region (measurement region) reaches the light receiving point R on the surface of the head. As a result, information on the amounts of received light $A(\lambda_1)$, $A(\lambda_2)$ and $A(\lambda_3)$ concerning the measurement portion S of the subject is gained particularly in the measurement region, where the measurement portion S is at the depth L/2 of which the length is half of the shortest distance connecting the light sending point T and the light receiving point R along the surface of the head of the subject from the middle point M of the shortest line L that connects the light sending point T and the light receiving point R along the surface of the head of the subject.

In addition, the optical imaging device for brain functions use a near-infrared spectrum analyzer, for example, in order to measure the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]), respectively, concerning a number of measurement portions in the brain (see Japanese Unexamined Patent Publication 2001-337033).

FIG. 13 is a block diagram schematically showing an example of the structure of a conventional near-infrared spectrum analyzer. In addition, FIG. 14 is a perspective diagram showing an example of the appearance of the near-infrared spectrum analyzer in FIG. 13. Here, for the purpose of simplicity, several optical fibers for sending light and several optical fibers for receiving light have been omitted.

A near-infrared spectrum analyzer 101 has a case 11 in rectangular parallelepiped form (70 cm×100 cm×120 cm, for example).

The inside of the case 11 is provided with: a light source driver (light emitting unit) 2 for emitting light; a light detector 3 for detecting light; an A/D 5; a control unit 21 for sending and receiving light; a control unit 22 for analysis; and a memory 23, and the outside of the case 11 is provided with: 16 light sending probes (light sending means) 12; 16 light receiving probes (light receiving means) 13; 16 optical fibers 14 for sending light; 16 optical fibers 15 for receiving light; a display device 26 having a monitor screen 26a; and a keyboard (input device) 27.

The light source driver 2 is a light source for sending light to the light sending probes 12, respectively, in response to a drive signal inputted from the control unit 21 for sending and receiving light and is made of semiconductor lasers LD1, LD2 and LD3 so as to emit near-infrared rays having three different wavelengths $\lambda_1$, $\lambda_2$ and $\lambda_3$, for example.

The light detector 3 detects near-infrared rays received by the light receiving probes 13, respectively, so as to output 16 light receiving signals (information on the amounts of received light) $A(\lambda_1)$, $A(\lambda_2)$ and $A(\lambda_3)$ to the control unit 21 for sending and receiving light through the A/D 5 and is made of photoelectric multipliers, for example.

The optical fibers 14 for sending light and the optical fibers 15 for receiving light are tubes having a diameter of 2 mm and a length of 2 m to 10 m and can convey near-infrared rays in the direction of the axis in such a manner that the near-infrared rays that have entered from one end pass through the inside and are emitted from the other end or vice versa.

One optical fiber for sending light 14 is connected to one probe 12 for sending light and one semiconductor laser LD1, LD2 or LD3 in the light source driver 2 at the two ends so that they are away from each other by a set length (2 m to 10 m).

One optical fiber for receiving light 15 is connected to one probe 13 for receiving light a id one photoelectric multiplier in the light detector 3 at the two ends so that they are away from each other by a set length (2 in to 10 m).

This near-infrared spectrum analyzer 101 uses a holder 130 in order to make the 16 light sending probes 12 and the 16 light receiving probes 13 make contact with the surface of the head of a subject in a predetermined alignment. FIG. 15 is a plan diagram showing an example of the holder 130 into which the 16 light sending probes and the 16 light receiving probes are inserted.

Light sending probes $12_{T1}$ to $12_{T16}$ and light receiving probes $13_{R1}$ to $13_{R16}$ are aligned alternately in a matrix of four rows and eight columns. Thus, the distance between the light sending probes and the light receiving probes 13 is constant, and information on the amounts of received light $A(\lambda_1)$, $A(\lambda_2)$ and $A(\lambda_3)$ is obtained at a certain depth from the surface of the head. Here, the distance between the probes is referred to as the channel length, and in general, channels are 30 mm. In the case where the channels are 30 mm, information on the amounts of received light $A(\lambda_1)$, $A(\lambda_2)$ and $A(\lambda_3)$ is obtained at a depth of 15 mm to 20 mm from the middle point of the channels. That, is to say, points at a depth of 15 mm to 20 mm from the surface of the head approximately correspond to portions on the surface of the brain, and thus, information on the amounts of received light $A(\lambda_1)$, $A(\lambda_2)$ and $A(\lambda_3)$ concerning the brain's activity is obtained.

Different numbers (T1, T2 . . . , R1, R2 . . . ) are allocated to through holes in the holder 130 so that it can be recognized which light sending probe $12_{T1}$ to $12_{T16}$ or light receiving probe $13_{R1}$ to $13_{R16}$ has been inserted into which through hole, and at the same time, different numbers (T1, T2 . . . ) are allocated to light sending probes $12_{T1}$ to $12_{T16}$, respectively, and different numbers (R1, R2 . . . ) are allocated to light receiving probes $13_{R1}$ to $13_{R16}$, respectively. As a result, the light sending probes $12_{T1}$ to $12_{T16}$ and the light receiving probes $13_{R1}$ to $13_{R16}$ are inserted into the through holes of the corresponding numbers, respectively.

In addition, the curvature on the surface of the head of a subject differs depending on the difference in the sex, age and individual valuations, and therefore, the holder 130 can easily fit on the face of a head even if the curvature is different, where the support portions for holding the light sending probes $12_{T1}$ to $12_{T16}$ and the light receiving probes $13_{R1}$ to $13_{R16}$ are aligned in grid form on the surface of the head, and at the same time, the support portions are connected with each other through flexible connection portions, and moreover, the connection portions are rotatable within a predetermined angle with the support portions as a rotational axis (see Japanese Unexamined Patent Publication 2002-143169).

As for the positional relationship between the 16 light sending probes $12_{T1}$ to $12_{T16}$ and the 16 light receiving probes $13_{R1}$ to $13_{R16}$, it is necessary to adjust the timing in which the light sending probes 12 emit light and the timing in which the light receiving probes 13 receive light so that one light receiving probe 13 does not simultaneously receive light emitted from a number of light sending probes 12, but receives only light emitted from one light transmitting probe 12. Therefore, a memory 23 stores a control table that indicates the timing in which the light source driver 2 emits light and the timing in which the light detector 3 detects light.

This control table is stored in the memory 23 in the control unit 21 for sending and receiving light, which outputs a drive signal for sending light to one light sending probe 12 to the light source driver 2 at a predetermined time, and at the same time, the light detector 3 detects a light receiving signal (information on the amount of received light) received by a light receiving probe 13.

As a result, a total of 52 pieces of information on the amounts of received light (S1 to S52) $A(\lambda_1)$, $A(\lambda_2)$ and $A(\lambda_3)$ is collected, as shown in the plan diagram of FIG. 15.

In addition, a control unit 22 for analysis finds the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) from the intensity of light having the respective wavelength (the wavelength absorbed by oxyhemoglobin and the wavelength absorbed by deoxyhemoglobin) that has passed through the optical path on the basis of the total of the 52 pieces of information on the amounts of received light $A(\lambda_1)$, $A(\lambda_2)$ and $A(\lambda_3)$ by using the simultaneous equations (1) to (3).

When a chronological change in the blood flow through portions in the brain of a subject while the subject is exercising, such as for rehabilitation, is attempted to be measured using the above-described near-infrared spectrum analyzer 101, a light sending probe $12_{T1}$ to $12_{T16}$ or a light receiving probe $13_{R1}$ to $13_{R16}$ may disengage from a through hole of the holder 130 because the case 11 with a size of 70 cm×100 cm×120 cm is fixed somewhere in a room. That is to say, the measurement procedure cannot be carried out when the movement of the subject is very active.

In addition, the time for a subject to exercise, such as for rehabilitation, is approximately one hour, and the time for a doctor to attach the holder 130 to the head of the subject and attach the light sending probes $12_{T1}$ to $12_{T16}$ and the light receiving probes $13_{R1}$ to $13_{R16}$ to the through holes of the holder 130 is also approximately one hour. That is to say, the preparation time during which the subject wears the holder 130 with the light sending probes $12_{T1}$ to $12_{T16}$ and the light receiving probes $13_{R1}$ to $13_{R16}$ on the head is very long as compared to the time during which the subject exercises, such as for rehabilitation.

Furthermore, the subject may exercise at home everyday, such as for rehabilitation, and it is almost impossible to provide the near-infrared spectrum analyzer 101 to every home, judging from the installment space and cost.

In addition, it is very troublesome for a family member to attach the holder 130 with the light sending probes $12_{T1}$ to $12_{R16}$ and the light receiving probes $13_{R1}$ to $13_{R16}$ to the head of the subject, and the subject alone cannot do this.

SUMMARY

In order to solve the above-described problems, the present inventors examined conventional optical measurement devices in order to develop one with which measurement is possible even when the movement of the subject is very active. Thus, it was found that in the case where a chronological change in the blood flow through portions in the brain of a subject was precisely measured (diagnosed), an optical measurement device having a large number of light sending probes and a large number of light receiving probes was necessary, but in the case where a chronological change in the blood flow through portions in the brain of a subject was measured when the subject exercised, such as for rehabilitation, it was sufficient to measure the chronological change in the blood flow through certain portions in the brain used during exercise, and thus, it was possible to use an optical measurement device having a small number of light transmitting probes and a small number of light receiving probes. As a result, it was found that it is possible to use two types of optical measurement devices: a main optical measurement device having a large number of light sending probes, a large number of light receiving probes and a case (70 cm×100 cm×120 cm, for example); and a portable optical measurement device having a small number of light sending probes, a small number of light receiving probes and a case (10 cm×10 cm×5 cm, for example). Thus, a subject can carry the portable optical measurement device because the number of probes of the portable optical measurement device is small, which makes the size of the case small, and as a result, measurement is possible even when the movement of the subject is very active.

Furthermore, in many cases, the subject exercises at home, such as for rehabilitation, and therefore, portable optical measurement devices were examined to develop one for which the subject alone can attach the holder with the light sending probes and the light receiving probes to his or her own head. In general holders used for the above-described near-infrared spectrum analyzer, the connection portions were flexible and rotatable within a predetermined angle with the support portions as a rotational axis, and thus, as possible to change the shape of the holder so that the holder could easily fit on the head even when the curvature on the surface of the head was different. Therefore, the shape of the holder changed, which made it difficult for the subject alone to attach the holder with the light sending probes and the light receiving probes to his or her own head. Thus, it was found that a specific holder should be selected from among various types of holders of which the form does not change or a holder dedicated to the subject should be manufactured so that the holder used for the portable optical measurement device fits on the head of the subject without the form of the holder changing, though it can only be used by the subject on whom the measurement process is carried out. It was also found that a specific holder should be selected from among various types of holders or a holder dedicated to the subject should be manufactured on the basis of the measurement data obtained at the time of diagnoses using the main optical measurement device so that a chronological change in the blood flow through certain portions in the brain of the subject can be measured without fail. As a result, the subject alone can attach the holder with the light sending probes and the light receiving probes on his or her own head, and the preparation time during which the holder is worn is very short.

That is to say, the optical measurement system according to the example of the present invention is an optical measurement system having a main optical measurement device and a portable optical measurement device, wherein the above-described main optical measurement device has: a first case; A first light sending means for irradiating a subject with light; B first light receiving means for receiving light emitted from the above-described subject; a display device; a first holder to be worn on the head of the above-described subject, to which at least (A+B) through holes are provided; and a control unit provided inside the above-described first case for controlling the above-described first light sending means and the above-described first light receiving means so as to obtain measurement data on the brain's activity and display the measurement data on the display device, and the above-described portable optical measurement device has: a second case that is portable by a subject; C second light sending means for irradiating the subject with light; D second light receiving means for receiving light emitted from the above-described subject; a second holder to be worn on the head of the above-described subject, to which at least (C+D) through holes are provided; a control unit provided inside the above-described second case for controlling the above-described second light sending means and the above-described second light receiving means so as to obtain measurement data on the brain's activity; and a communication unit that can communicate with the above-described main optical measurement device, wherein (C+D)<(A+B) is satisfied, and the communication unit of the above-described portable optical measurement device transmits the measurement data obtained by the control unit of the above-described portable optical measurement device to the main optical measurement device.

Here, the word "portable" means that the subject can wear the device, and the device can be put into a pocket, worn on the subject's back like a backpack, or put into a waist bag. Therefore, it is preferable for the size of the second case to be 10 cm$^3$ or more and 20 cm$^3$ or less.

In addition, the communication unit can transmit the measurement data obtained by the control unit of the portable optical measurement device to the main optical measurement device, and real time communication may be possible by means of wires or a wireless system, or data may be transferred out to the main optical measurement device from the portable optical measurement device using a portable memory, for example.

As described above, in the examples of the optical measurement system according to the present invention, (C+D) is smaller than (A+B), and it is not necessary for the portable optical measurement device to be provided with a display device, which makes it possible to reduce the size of the second case, and therefore, the subject can carry the portable optical measurement device, and as a result, measurement is possible even when the movement of the subject is very active.

In other examples of the optical measurement system according to the present invention, the second holder used for the above-described portable optical measurement device may be selected or fabricated on the basis of the measurement data obtained by the control unit of the above-described main optical measurement device.

In the further examples of the optical measurement system according to the present invention, only (C+D) through holes are provided in the second holder, but the second holder with which a chronological change in the blood flow through certain portions in the brain of the subject can be measured without fail can be selected or fabricated. As a result, the subject alone can attach the second holder with the second light sending means and the second light receiving means to his or her own head, and the preparation time during which the second holder is worn is very short. Accordingly, the chronological change in the blood flow through the portions in the brain of the subject can be easily measured when the subject is exercising, such as for rehabilitation.

In the examples of the optical measurement system according present invention, the measurement data obtained by the control unit of the above-described portable optical measurement device may be data when the above-described subject is exercising, while the measurement data obtained by the control unit of the above-described main optical measurement device may be data the above-described subject is at rest.

In further examples of the optical measurement system according to the present invention, the main optical measurement device can be used in the case where the chronological change in the blood flow through the portions in the brain of the subject is measured (diagnosed) precisely, while the portable optical measurement device can be used in the case where the chronological change in the blood flow through the portions in the brain of the subject is measured when the subject is exercising, such as for rehabilitation.

The examples of the optical measurement system may further have an analysis device, which is provided with a display device and a control unit for displaying the above-described measurement data on the display device, where the above-described portable optical measurement device has a communication unit that can communicate with the above-described analysis device, and the communication unit in the above-described portable optical measurement device transmit measurement data obtained by the control unit of the above-described portable optical measurement device to the analysis device.

In the examples, the portable optical measurement device can be used without the main optical measurement device as long as the analysis device is available. Accordingly, measurement is possible even when the subject exercises at home, such as for rehabilitation.

In addition, the present example provides a portable optical measurement device used in the above-described optical measurement system, which is further provided with a control unit for obtaining measurement data on brain activities and a communication unit that can communicate with the above-described main optical measurement device, wherein the above-described communication unit transmits the measurement data obtained by the above-described control unit to the main optical measurement device.

Furthermore, in the portable optical measurement device example, the above-described communication unit may transmit the measurement data when the above-described subject is exercising to the main optical measurement device.

Moreover, the examples of the present invention provide a rehabilitation planning method using the above-described optical measurement system, which includes: a main optical measurement device using step of obtaining measurement data when a subject is at rest by means of the control unit of the main optical measurement device; a diagnosing step of diagnosing the subject by checking the measurement data obtained in the above-described main optical measurement device using step; a portable optical measurement device using step of obtaining measurement data when the subject is exercising by means of the control unit of the portable optical measurement device; and a determination step of determining whether the main optical measurement device using step or the portable optical measurement device using step is carried out by checking the measurement data obtained in the above-described portable optical measurement device using step.

DETAILED DESCRIPTION

In the following, examples of the present invention are described in reference to the drawings. Here, the examples of the present invention are not limited to the below-described examples, but various modifications are, of course, included as long as the gist of the present invention is not deviated from.

Figure 1:
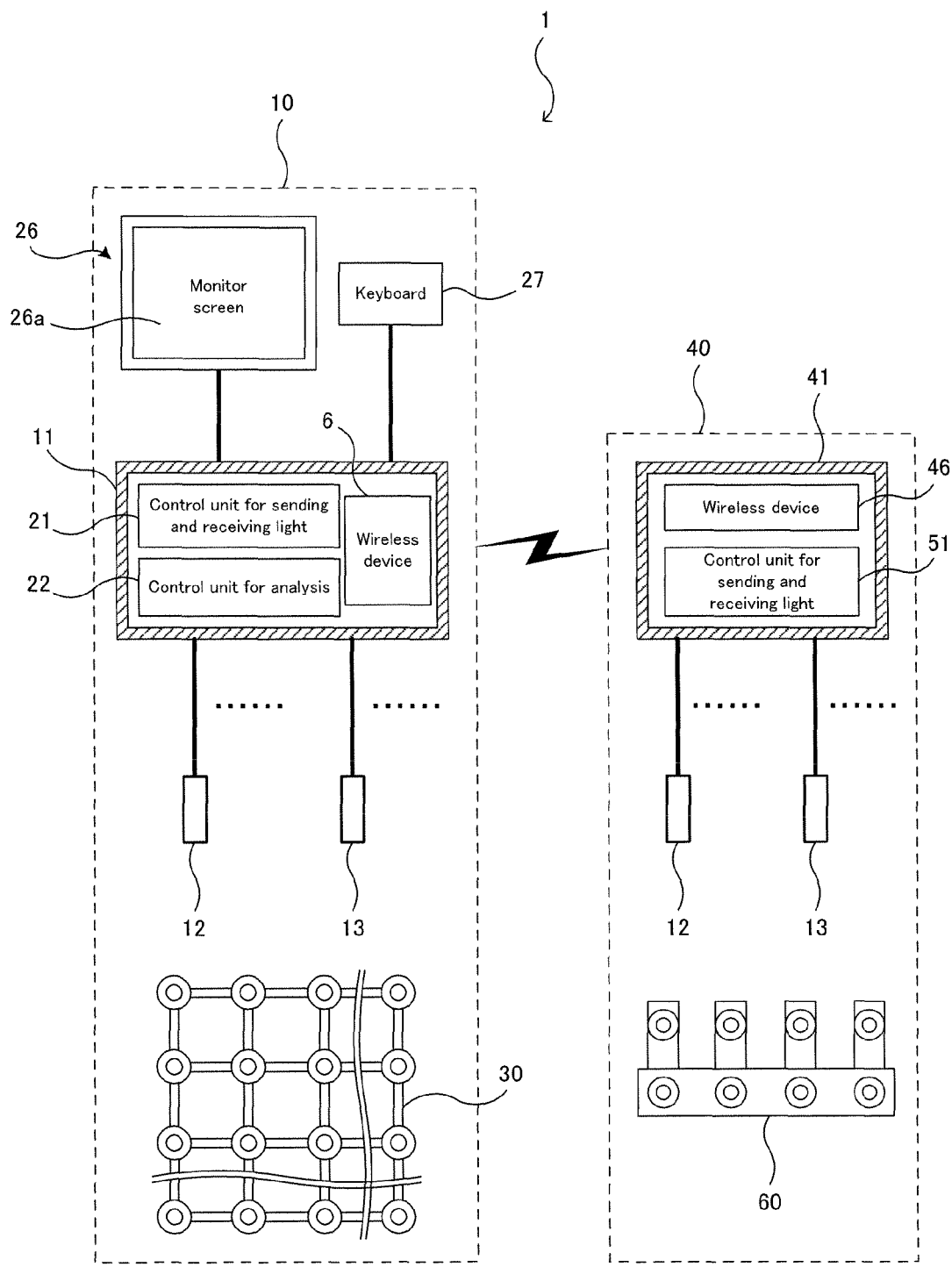
FIG. 1 is a block diagram schematically showing an example of the structure of the optical measurement system according to one embodiment of the present invention.
Figure 2:
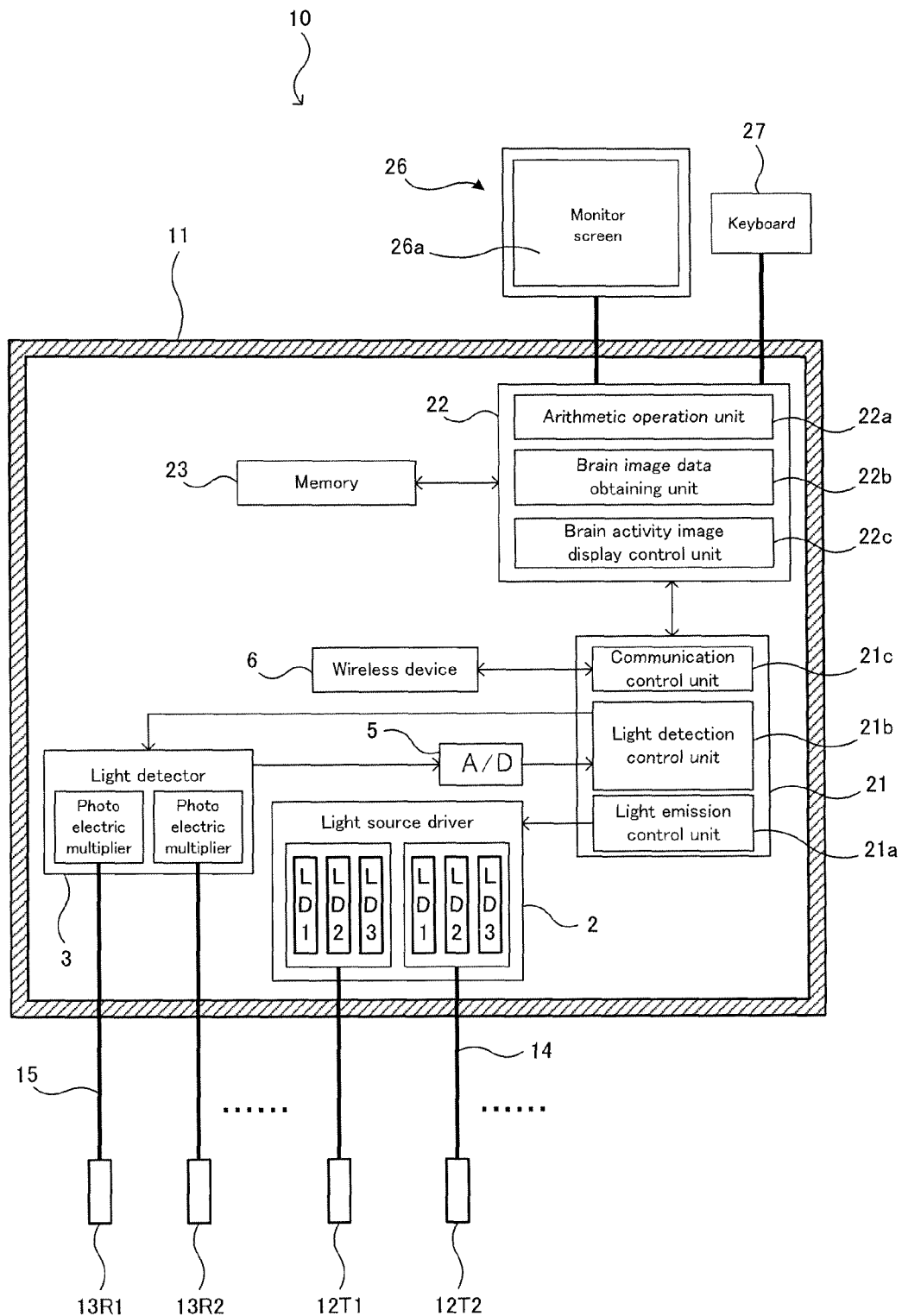
FIG. 2 is a block diagram schematically showing the structure of the main optical measurement device in FIG. 1.
Figure 3:
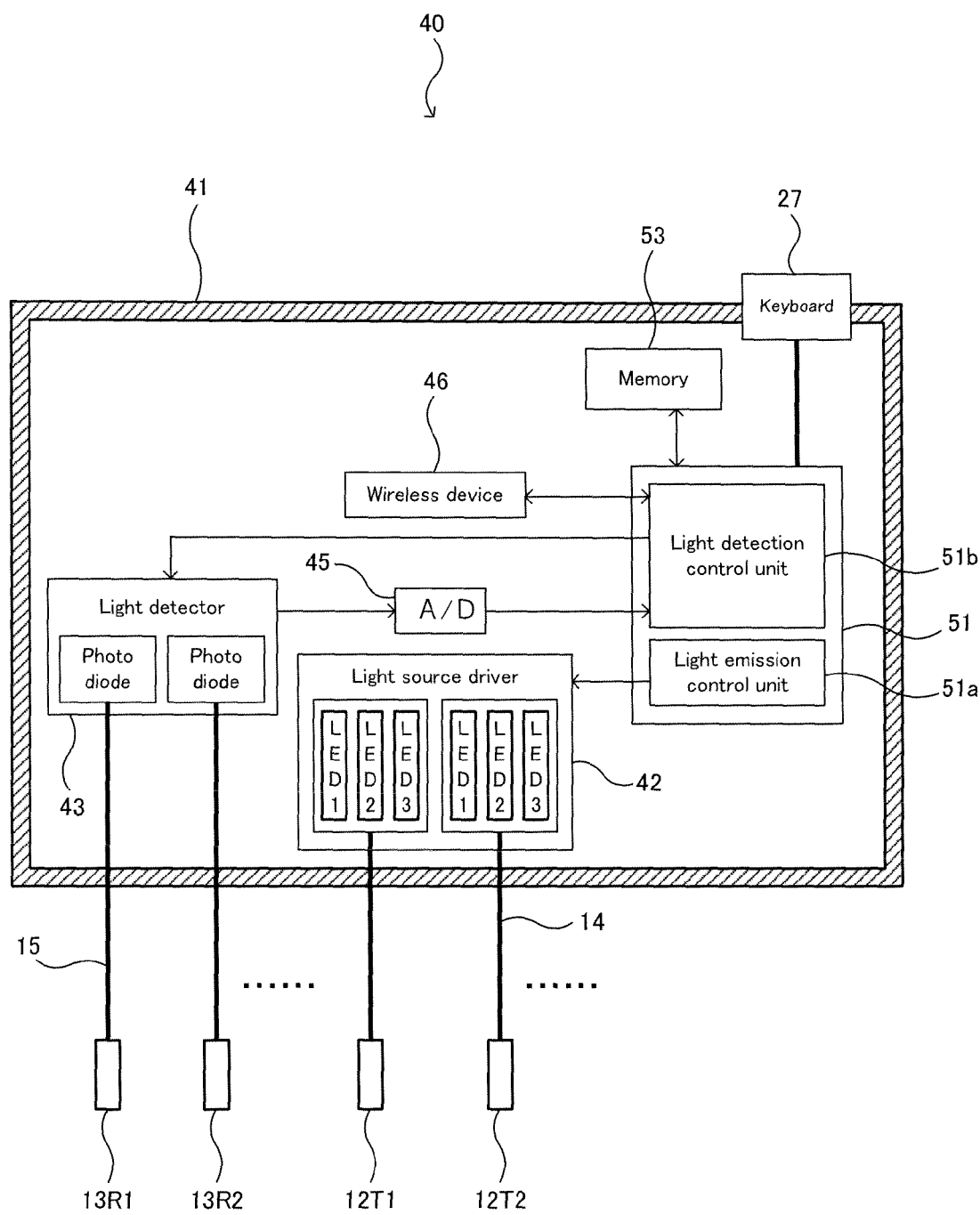
FIG. 3 is a block diagram schematically showing the structure of the portable optical measurement device in FIG. 1.
Figure 4:
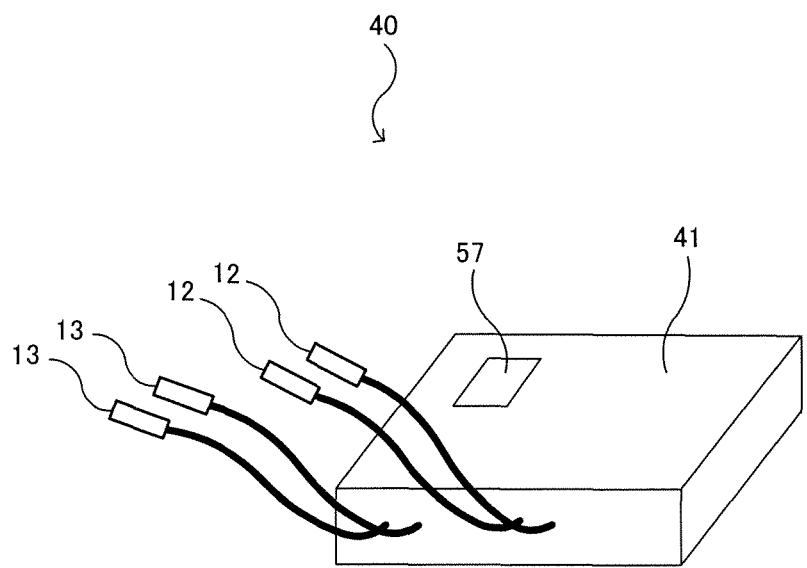
FIG. 4 is a perspective diagram showing the appearance of an example of the portable optical measurement device.

FIG. 1 is a block diagram schematically showing the structure of the optical measurement system according to an example of the present invention. FIG. 2 is a block diagram schematically showing the structure of the main optical measurement device in FIG. 1, and FIG. 3 is a block diagram schematically showing the structure of the portable optical measurement device in FIG. 1. In addition, FIG. 4 is a perspective diagram showing appearance of an example of the portable optical measurement device.

Figure 6:
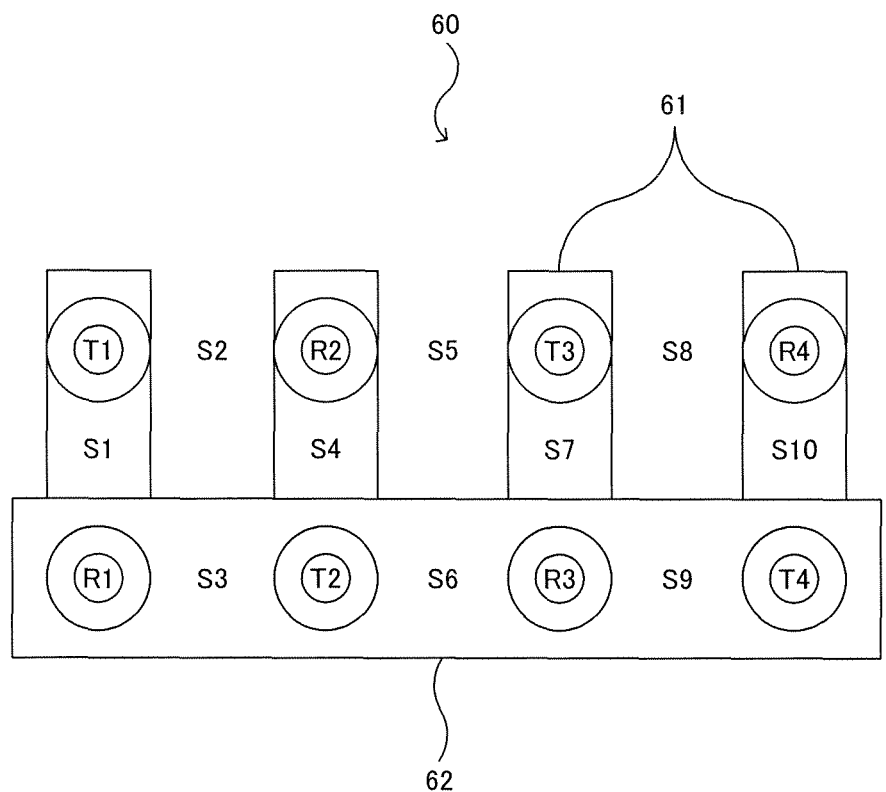
FIG. 6 is a plan diagram showing an example of the second holder into which four light sending probes and four light receiving probes are inserted.
Figure 5:
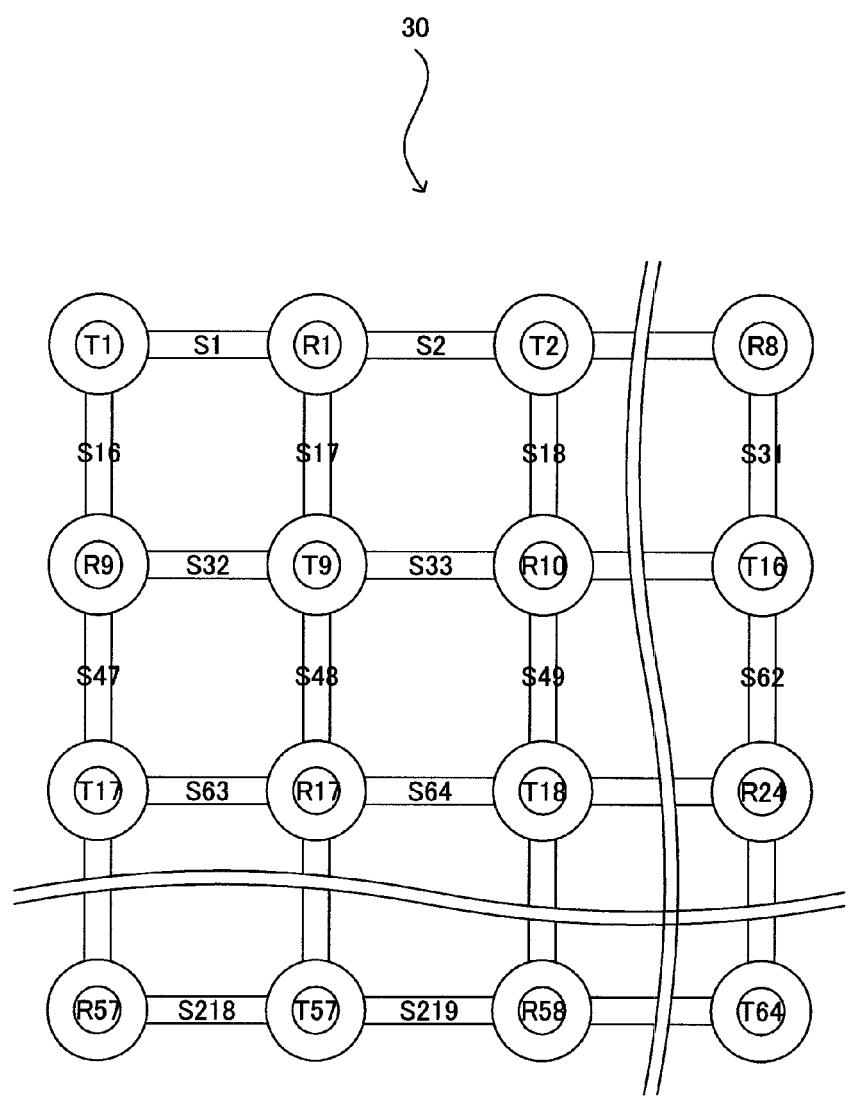
FIG. 5 is a plan diagram showing an example of the first holder into which 64 light sending probes and 64 light receiving probes are inserted.

Furthermore, FIG. 5 is a plan diagram showing an example of the first holder into which 64 light sending probes and 64 light receiving probes are inserted, and FIG. 6 is a plan diagram showing an example of the second holder into which four light sending probes and four light receiving probes are inserted.

An optical measurement system 1 is provided with one main optical measurement device 10 having a first holder 30 and one portable optical measurement device 40 having a second holder 60. Here, the same symbols are attached to the same components as in the near-infrared spectrum analyzer 101.

In an example, the main optical measurement device 10 and the portable optical measurement device 40 are installed in a hospital.

Figure 7:
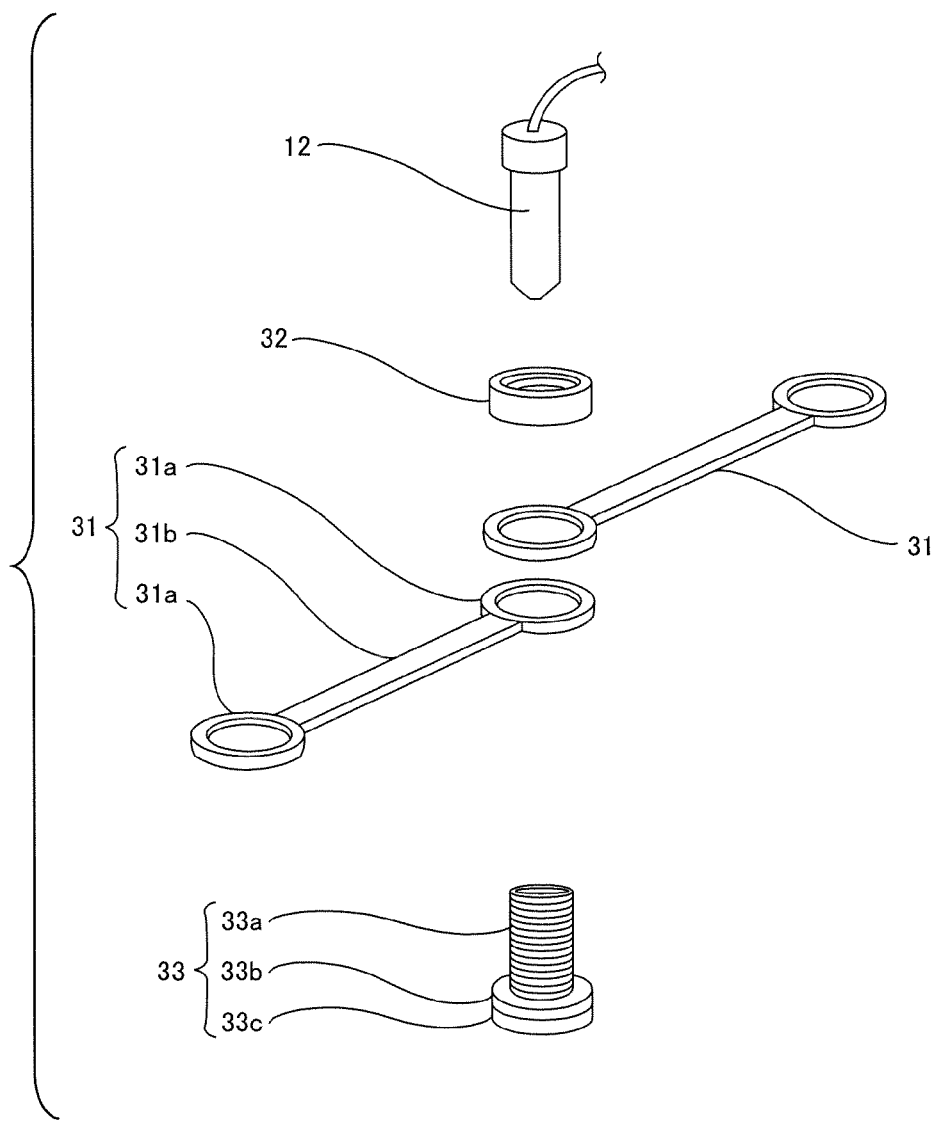
FIG. 7 is an exploded perspective diagram showing a light sending probe, a nut, two connection parts and a socket.

First, the first holder 30 is described. FIG. 7 is an exploded perspective diagram showing a light sending probe 12, a nut 32, two connection parts 31 and a socket 33, and FIG. 8 is a diagram showing the light sending probe 12, the nut 32, the two connection parts 31 and the socket 33 after assembly.

The first holder 30 is provided with 128 sockets 33 for securing a light sending probe 12 or a light receiving probe 13 and 232 connection parts 31 and 128 nuts 32.

The connection parts 31 are plates in linear form. In addition, the connection parts 31 have insertion portions 31a in ring form at the two ends and a linking portion 31b having a channel length X for linking the two insertion portions 31a at the two ends. A circular through hole through which a socket 33 is inserted is created at the center of each insertion portion 31a. In addition, the linking portions 31b have a width of 10 mm and a thickness of 0.1 mm, where the distance between the centers of the through holes is 30 mm, which is the channel length, and thus have flexibility only in the direction of the thickness. That is to say; the insertion portions 31a at the two ends are always held to maintain the same channel length X.

The sockets 33 have a main body 33a in cylindrical form, a flange 33b in ring form and a bottom 33c in ring form so that a light sending probe 12 or a light receiving probe 13 can be inserted inside, and the outer surface of the main body 33a is threaded with which a nut 32 is engaged.

The nuts 32 are in ring form having a circular through hole, inside which is threaded so as to be engaged with the main body 33a of a socket 33. Here, the size of the through holes is greater than the size of the main body 33a of a socket 33 as viewed from the top and is smaller than the flange 33b of a socket 33.

As a result, the main body 33a of a socket 33 is screwed inside a nut 32 so that an insertion portion 31a of a connection part 31 can be sandwiched between the flange 33b of the socket 33 and the nut 32 so as to be secured. At this time, one connection part 31 may be secured by sandwiching an insertion portion 31a of the connection part 21 between the flange 33b of the socket 33 and the nut 32. Meanwhile, four connection parts 31 may be secured by sandwiching the insertion portions 31a of the four connection parts 31 between the flange 33b of the socket 33 and the nut 32. That is to say, any number of connection parts 31 can be secured.

Figure 8A:
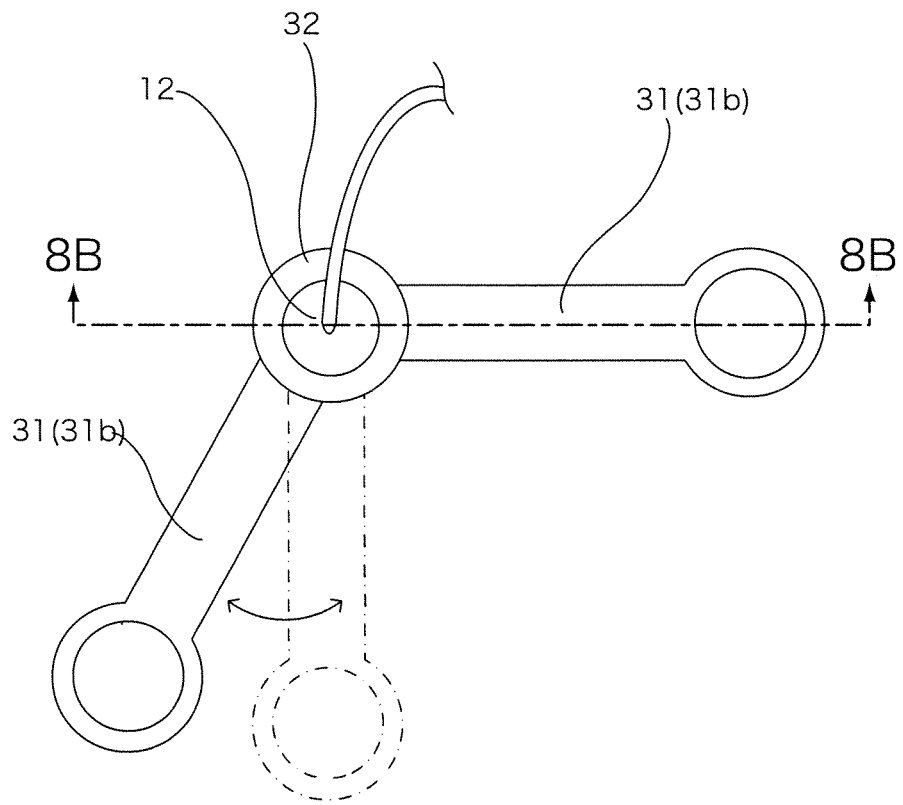
FIGS. 8A and 8B are diagrams showing the light sending probe, the nut, the two connection parts and the socket after assembly.
Figure 8B:
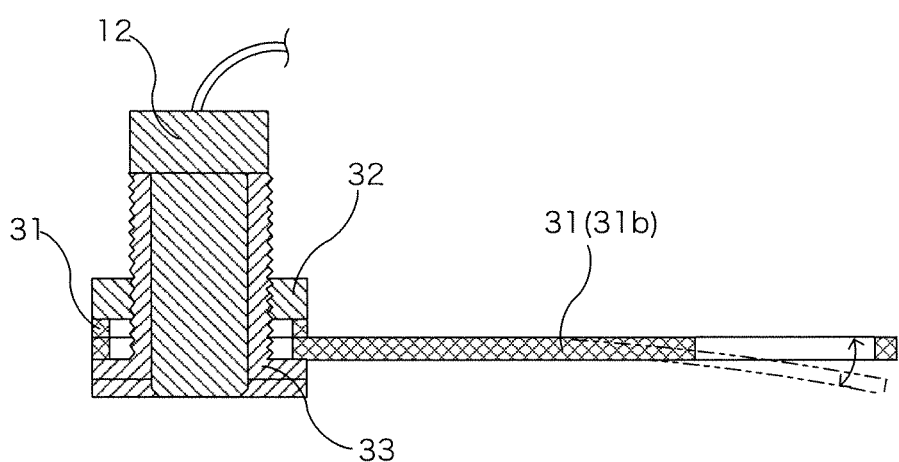

Thus, 128 sockets 33, 232 connection parts 31 and 128 nuts 32, for example, are used to fabricate a first holder 30 as in FIG. 5. This first holder 30 can be worn on a head, which makes close contact with the surface of the head, as one connection part 31 and another connection part 31 can form a desired angle with a socket 33 as an axis as viewed from the top when secured as shown in FIG. 8A, and the linking portion 31b of the connection parts 31 has flexibility as in FIG. 8B so as to be changed into such a form as to have the same curvature as the surface of the head. FIG. 8B is a cross-sectional view taken on line A-A of FIG. 8A. At this time, the angles between the connection parts 31 can be fixed in such a state that the form of the linking portions 3 lb are changed, and thus, the curvature can be maintained.

Here, at the time of measurement, light sending probes $12_{T1}$ to $12_{T64}$ and light receiving probes $13_{R1}$ to $13_{R64}$ are respectively inserted into the sockets 33 having the corresponding numbers.

The main optical measurement device 10 has a first case 11 in rectangular parallelepiped form (70 cm×100 cm×120 cm for example).

The inside of the first case 11 is provided with a light source driver (first light emitting unit) 2 for emitting light, a light detector (first light detecting unit) 3 for detecting light, an A/D 5, a wireless device (communication unit) 6 for wirelessly communicating with the control unit 51 for sending and receiving light of the portable optical measurement device 40, a control unit 21 for sending and receiving light, a control unit 22 for analysis and a memory 23, and at the same time, the outside of the first case 11 is provided with 64 (A) light sending probes (first light sending means) $12_{T1}$ to $12_{T64}$, 64 (B) light receiving probes (first light receiving means) $13_{R1}$ to $13_{R64}$, 64 (A) optical fibers 14 for sending light, 64 (B) optical fibers 15 for receiving light, a display device 26 having a monitor screen 26a and a keyboard (input device) 27.

Thus, the main optical measurement device 10 is provided with 64 light sending probes $12_{T1}$ to $12_{T64}$ and 64 light receiving probes $13_{R1}$ to $13_{R64}$ so that a chronological change in the blood flow through some portions in the brain of a subject can be precisely measured (diagnosed).

The light sending probes $12_{T1}$ to $12_{T64}$ are in long, cylindrical form with the upper end slightly thicker for fixation to a socket 33. In addition, the upper end of the light sending probes $12_{T1}$ to $12_{T64}$ is connected to the light source driver 2 through an optical fiber 14 for sending light so that light can be emitted from the lower end.

The light receiving probes $13_{R1}$ to $13_{R64}$ are also in long, cylindrical form with the upper end slight thicker, like the light sending probes $12_{T1}$ to $12_{T64}$. In addition, the upper end of the light receiving probes $13_{R1}$ to $13_{R64}$ is connected to the light detector 3 through an optical fiber 15 for receiving light so that the lower end can receive light.

The functions resulting from the process by the control unit 21 for sending and receiving light are described in the blocks in FIG. 2. The control unit 21 for sending and receiving light has a light emission control unit 21a for outputting a drive signal to the light source driver 2, a light detection control unit 21b for storing a light receiving signal (information on the amount of received light) $A(\lambda_1)$, $A(\lambda_2)$ and $A(\lambda_3)$ in a memory 23, and a communication control unit 21c for controlling the wireless device 6.

Upon reception of a start signal "diagnosis" from the keyboard 27, the light emission control unit 21a controls the system so that a drive signal for sending light to the light sending probes $12_{T1}$ to $12_{T64}$ is outputted to the light source driver 2 on the basis of the control table stored in the memory 23.

Upon reception of a start signal "diagnosis" from the keyboard 27, the light detection control unit 21b controls the system so that the information on the amount of received light $A(\lambda_1)$, $A(\lambda_2)$ and $A(\lambda_3)$ from the light detector 3 is stored in the memory 23 on the basis of the control table stored in the memory 23.

Upon reception of a start signal "rehabilitation" from the keyboard 27, the communication control unit 21c receives the information on the amount of received light $A(\lambda_1)$, $A(\lambda_2)$ and $A(\lambda_3)$ gained in the control unit 51 for sending and receiving light in the below-described portable optical measurement device 40 through the wireless device 6 and controls the system so that the information on the amount of received light $A(\lambda_1)$, $A(\lambda_2)$ and $A(\lambda_3)$ is stored in the memory 23.

The functions resulting from the process by the control unit 22 for analysis are described in the blocks in FIG. 2. The control unit 22 for analysis has an arithmetic operation unit 22a, a brain image data obtaining unit 22b for obtaining brain image data of a subject, and a brain activity image display control unit 22c.

The brain image data obtaining unit 22b controls the system so that the brain image data of a subject is obtained and stored in the memory 23. Before measurement, an image of a subject is taken by a magnetic resonance imaging apparatus (hereinafter abbreviated as MRI), for example, so that brain image data is prepared. Thus, the brain image data from the MRI is stored in the memory 23.

The arithmetic operation unit 22a controls the system so that the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) are found from the intensity of light having the respective wavelength (the wavelength absorbed by oxyhemoglobin and the wavelength absorbed by deoxyhemoglobin) that has passed through the optical path on the basis of the information on the amount of received light $A(\lambda_1)$, $A(\lambda_2)$ and $A(\lambda_3)$ stored in the memory 23 using the simultaneous equations (1), (2) and (3).

The brain activity image display control unit 24c controls the system so that information is displayed on the monitor screen 26a. Contour graphs of the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) in planes of the brain, for example, are displayed on the brain image data. At this time, the contour graphs are displayed on the entire surface of the brain when the measurement data obtained by the control unit 21 for sending and receiving light is displayed, while the contour graphs are displayed on part of the brain when the measurement data obtained by the control unit 51 for sending and receiving light is displayed.

The second holder 60 is a plate in comb form where four linear branches 61 having a predetermined width (10 mm, for example) are aligned parallel to each other with spaces in between (30 mm, for example), and one linear base 62 is provided to connect one end of these branches 61 together.

In addition, circular through holes are created at the end of the branches 61, and at the same time, circular through holes are created in the locations of the base 62, which are away from the through holes in the branches by the channel length X (30 mm, for example). At this time, the through holes created in the base 62 are also away from each other by the channel length X (30 mm, for example).

The second holder 60 is fabricated so as to be used only for the subject on which measurement is to be carried out, and thus, the subject can attach it to his or her own head.

Here, at the time of measurement, the light sending probes $12_{T1}$ to $12_{T4}$ and the light receiving probes $13_{R1}$ to $13_{R4}$ of the portable optical measurement device 40 are respectively inserted into the through holes having the corresponding numbers.

The portable optical measurement device 40 has a second case 41 in rectangular parallelepiped form (10 cm×10 cm×5 cm, for example). Accordingly, the subject can carry portable optical measurement device 40 in a pocket or the like.

The inside of the second case 41 is provided with a light source driver (second light emitting unit) 42 for emitting light, a light detector (second light detecting unit) 43 for detecting light, an A/D 45, a wireless device (communication unit) 46 for wirelessly communicating with the control unit 21 for sending and receiving light of the main optical measurement device 10, a control unit 51 for sending and receiving light, and a memory 53, and at the same time, the outside of the second case 41 is provided with four (C) light sending probes (second light sending means) $12_{T1}$ to $12_{T4}$, four (D) light receiving probes (second light receiving means) $13_{R1}$ to $13_{R4}$, four (C) optical fibers 14 for sending light, four (D) optical fibers 15 for receiving light, and a switch (input device) 57 for turning ON/OFF the portable optical measurement device 40.

The light source driver 42 is a light source for sending light to the light sending probes $12_{T1}$ to $12_{T4}$, respectively, in response to a drive signal inputted from the control unit 51 for sending and receiving light, and is made of light emitting diodes LED1, LED2 and LED3 that can emit near-infrared rays having three different wavelengths $\lambda_1$, $\lambda_2$ and $\lambda_3$, for example. Because of the light emitting diodes LED1, LED2 and LED3, the second case 41 can be made more compact.

The light detector 43 is a detector for detecting the near-infrared rays received by the light receiving probes $13_{R1}$ to $13_{R4}$, respectively and thus outputting four light receiving signals (information on the amount of received light) $A(\lambda_1)$, $A(\lambda_2)$ and $A(\lambda_3)$ to the control unit 51 for sending and receiving light via the A/D 45, and is made of a photodiode, for example. Because of the photodiode, the second case 41 can be made more compact.

The functions resulting from the process by the control unit 51 for sending and receiving light are described in the blocks in FIG. 3. The control unit 51 for sending and receiving light has a light emission control unit 51a for outputting a drive signal to the light source driver 42 and a light detection control unit 51b for transmitting light receiving signals (information on the amount of received light) $A(\lambda_1)$, $A(\lambda_2)$ and $A(\lambda_3)$ via the wireless device 46 upon reception of the light receiving signals from the light detector 43.

Upon reception of a start signal from the switch 57, the light emission control unit 51a controls the system so that a drive signal for sending light to the light sending probes $12_{T1}$ to $12_{T4}$ is outputted to the light source driver 42 on the basis of the control table stored in the memory 53.

Upon reception of a start signal from the switch 57, the light detection control unit 51b controls the system so that the information on the amount of received light $A(\lambda_1)$, $A(\lambda_2)$ and $A(\lambda_3)$ from the light detector 43 is transmitted via the wireless device 46 on the basis of the control table stored in the memory 53.

Next, a method for selecting or fabricating the second holder 60 that is used only for the subject on which measurement is carried out in the optical measurement system 1 is described. Though only eight through holes are provided in the second holder 60 in the optical measurement system 1, the second holder 60 is selected or fabricated so that a chronological change in the blood flow through certain portions in the brain of the subject can be measured without fail.

Figure 9:
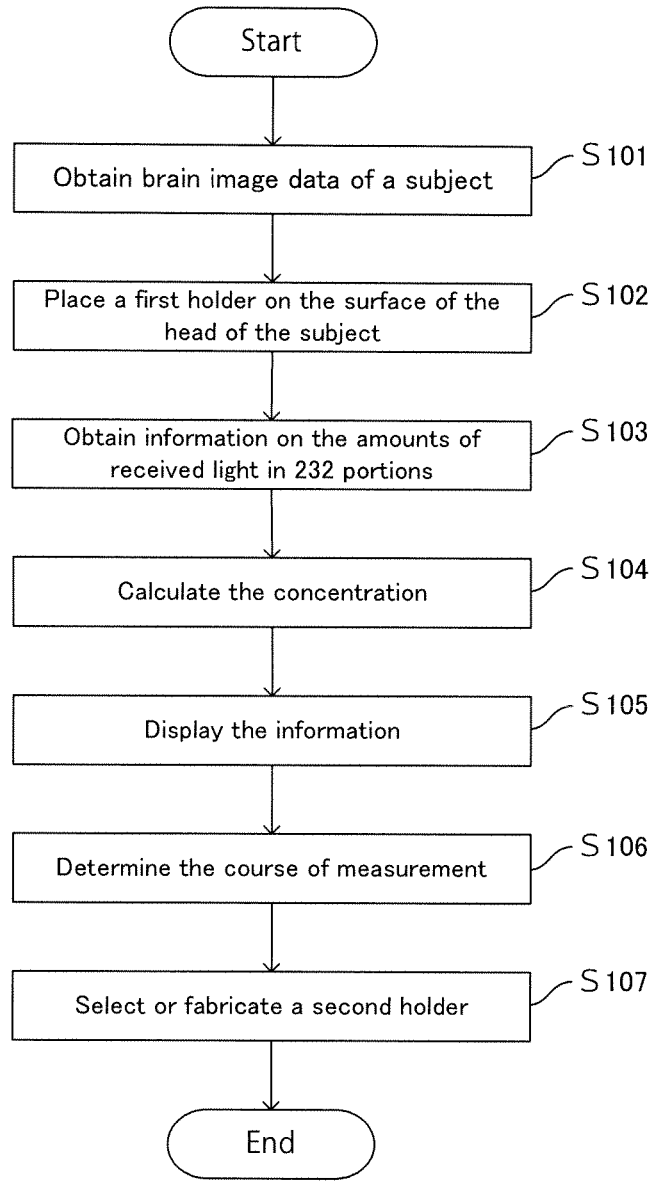
FIG. 9 is a flow chart for illustrating an example of the method for selecting the second holder in the optical measurement system.

FIG. 9 is a flow chart for illustrating an example of the method for selecting the second holder 60 in the optical measurement system 1.

First, in the process in step S101, a doctor or the like takes brain image data of the subject by means of an MRI, and the brain image data obtaining unit 22d obtains the brain image data of the subject from the MRI and stores it in the memory 23.

Next, in the process in step S102, the doctor or the like places the first holder 30 with the light sending probes $12_{T1}$ to $12_{T64}$ and the light receiving probes $13_{R1}$ to $13_{R64}$ on the surface of the head of the subject. At this time, it takes approximately one hour.

Next, in the process in step S103, the doctor or the like inputs a start signal "diagnosis" using the keyboard 27 so that the control unit 21 for sending and receiving light outputs a drive signal to the light source driver 2, and at the same time, receives a light receiving signal from the light detector 3 and stores the light receiving signal (information on the amount of received signal) $A(\lambda_1)$, $A(\lambda_2)$ and $A(\lambda_3)$ in the memory 23 (main optical measurement device using step). That is to say, information on the amount of received light from 232 portions $A(\lambda_1)$, $A(\lambda_2)$ and $A(\lambda_3)$ is stored in the memory 23.

Next, in the process in step S104, the arithmetic operation unit 24b finds the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) from the intensity of light having the respective wavelengths that has passed through the optical path on the basis of the information on the amount of received light $A(\lambda_1)$, $A(\lambda_2)$ and $A(\lambda_3)$ that is being stored in the memory 23 using the simultaneous equations (1), (2) and (3).

Next, in the process in step S105, the brain activity image display control unit 24c displays information on the monitor screen 26a. At this time, contour graphs are displayed on the entire surface of the brain.

Next, in the process in step S106, the doctor or the like determines the course of measurement for designating certain portions in the brain of the subject that are desired to carry out measurement while the subject is exercising, such as for rehabilitation, the shape of the holder, the number of used probes and the locations of the probes, and the period of time for rehabilitation, while checking the information displayed on the monitor screen 26a (diagnosis step).

Next, in the process in step S107, the designer or the like for selecting or fabricating the second holder 60 selects the second holder 60 from among various types of holders or fabricates a new second holder 60 on the basis of the course of measurement determined by the doctor or the like.

Finally, when the process in step S107 is completed, this flow chart is completed.

Figure 10:
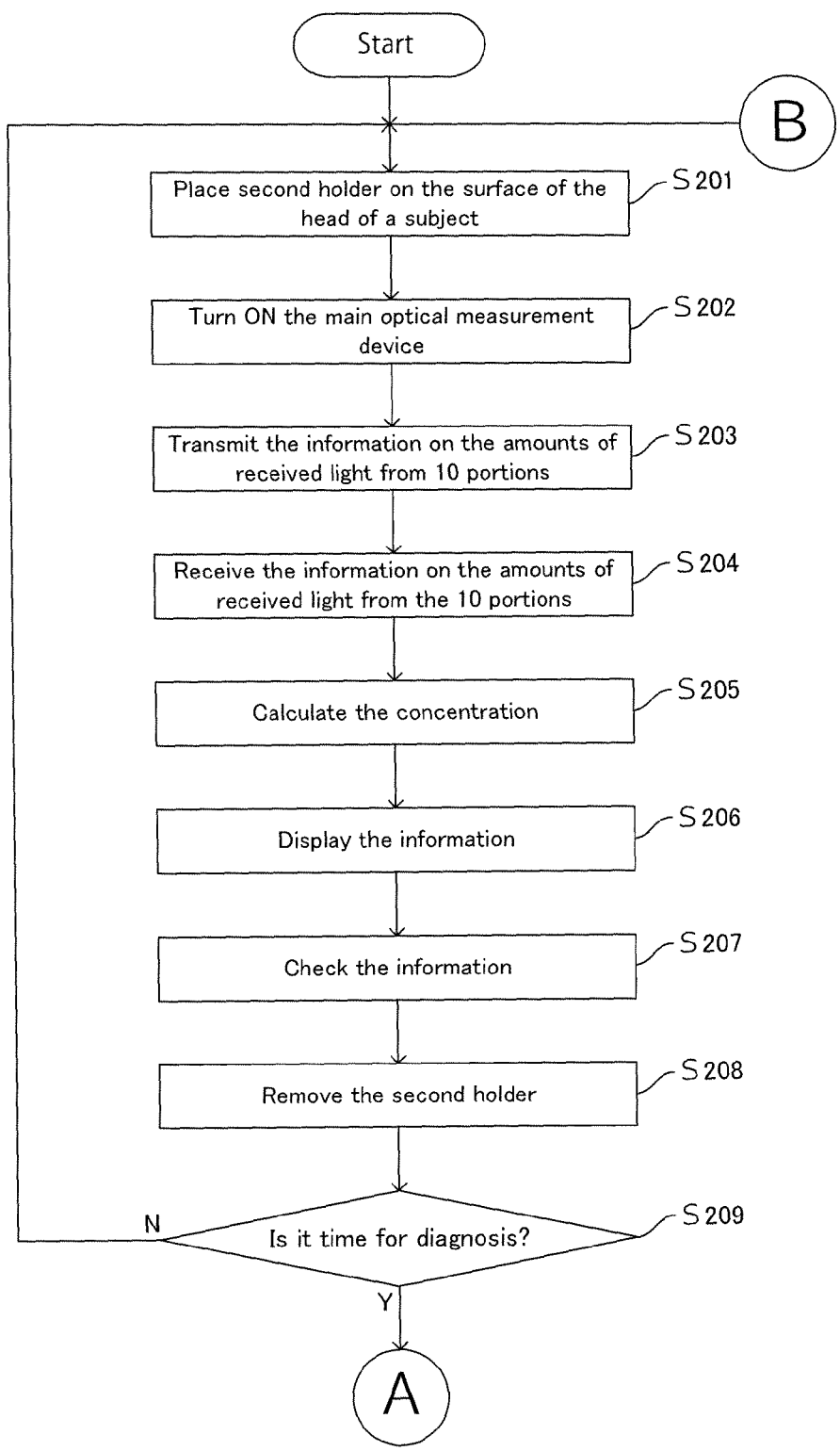
FIG. 10 is a flow chart for illustrating an example of the examination method in the optical measurement system.
Figure 11:
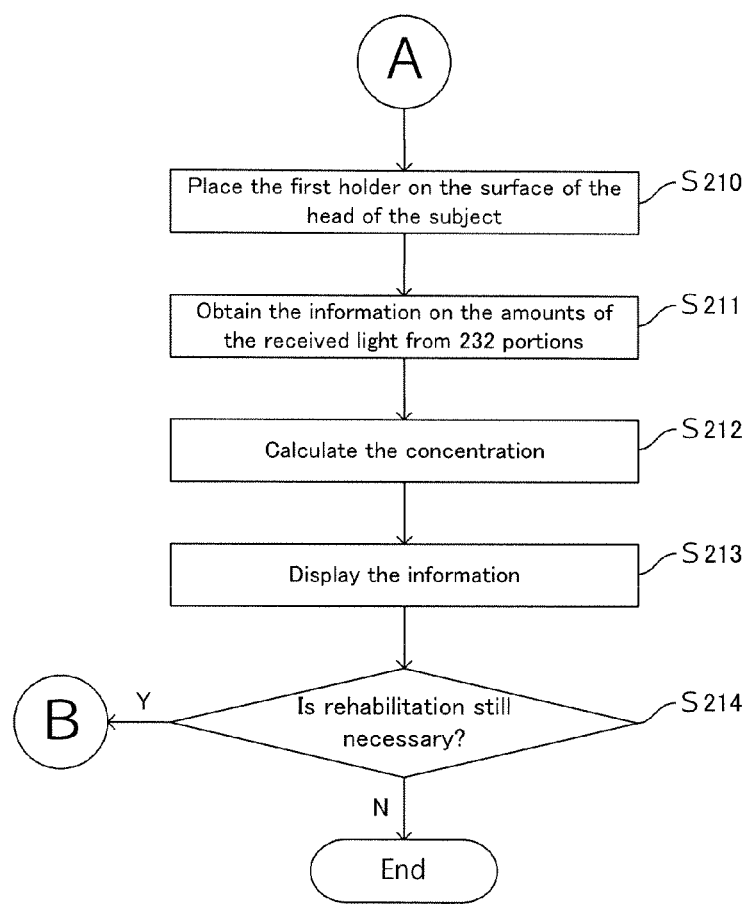
FIG. 11 is a flow chart for further illustrating the example of the examination method in the optical measurement system.
Figure 12A:
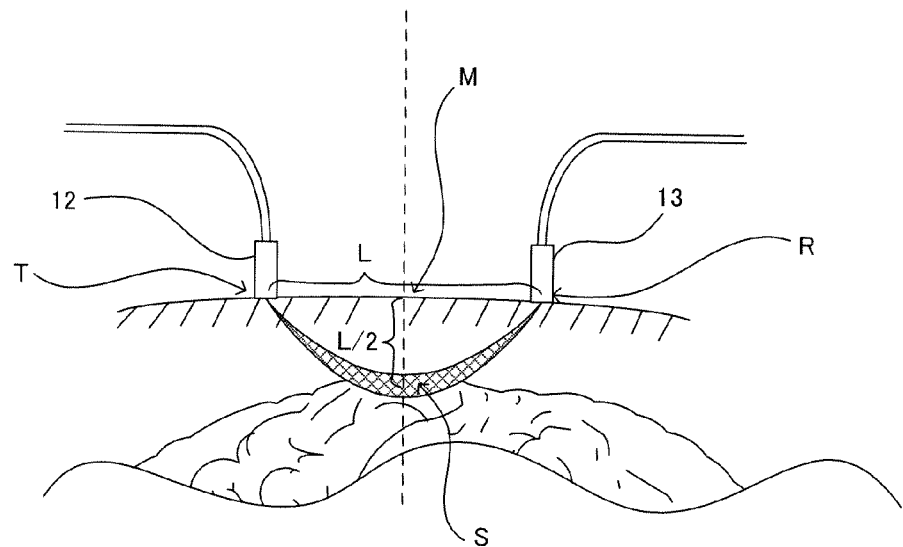
FIGS. 12A and 12B are diagrams showing the relationship between a pair of probes, a light sending probe and a light receiving probe, and a measurement portion.
Figure 12B:
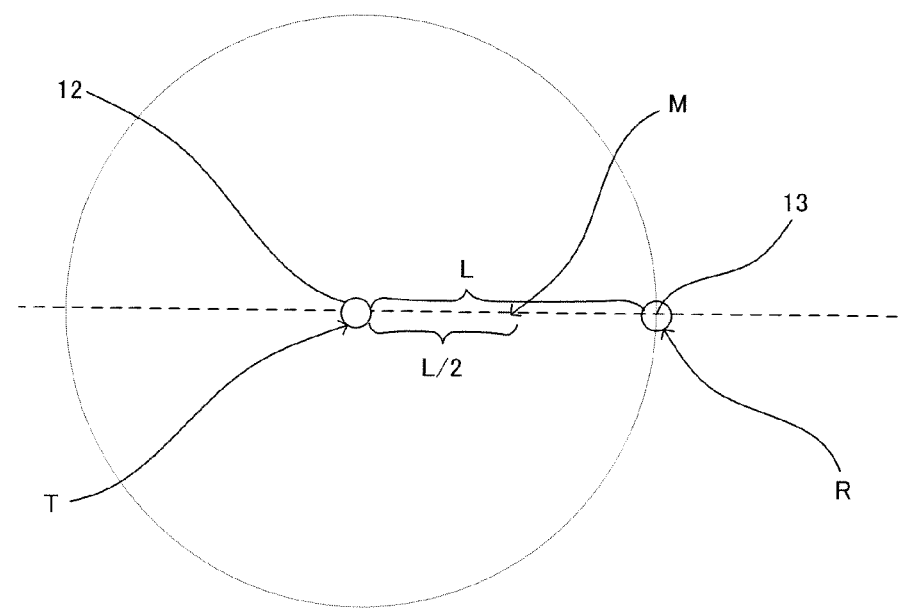
Figure 13:
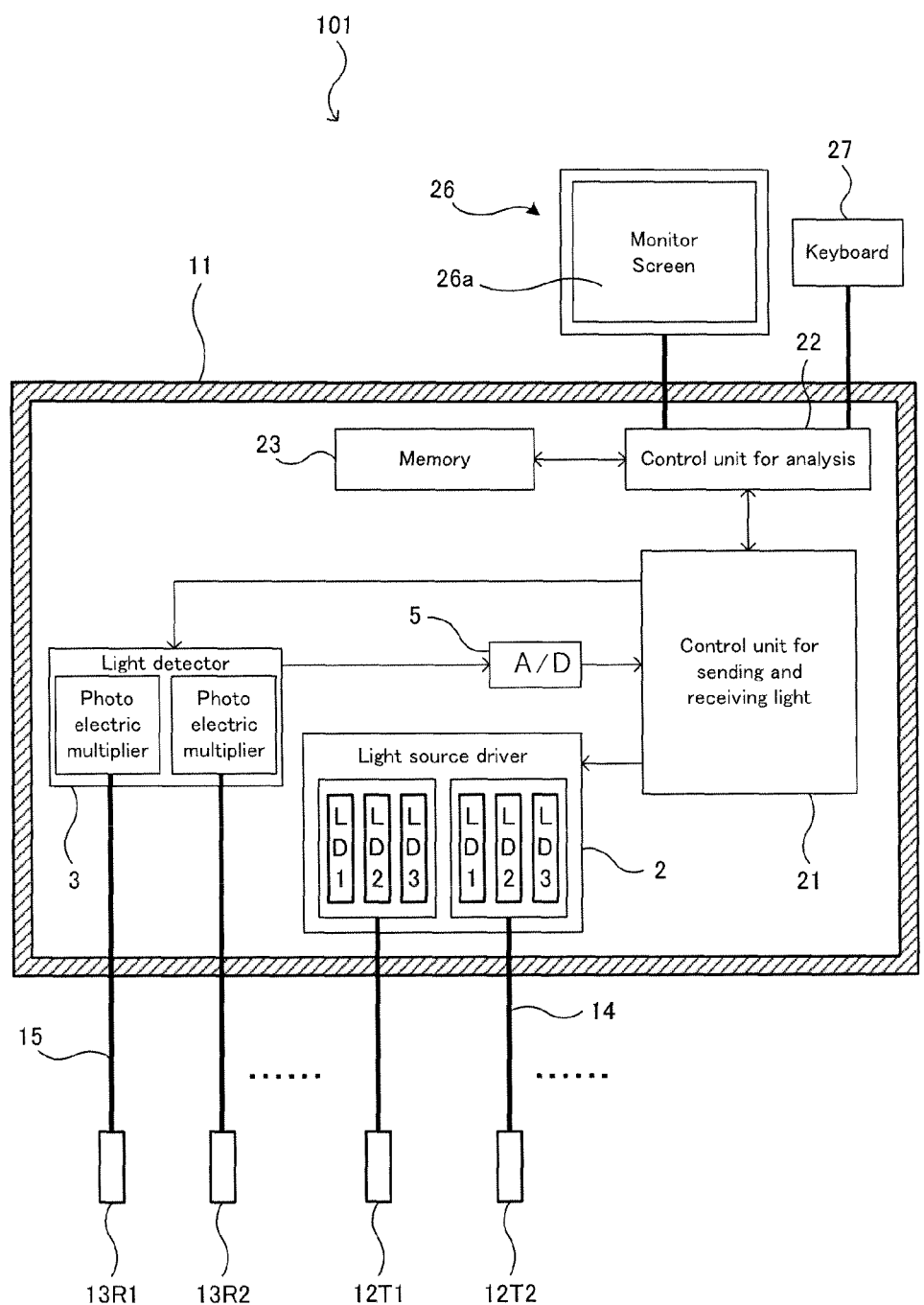
FIG. 13 is a block diagram schematically showing an example of the structure of a conventional near-infrared spectrum analyzer.
Figure 14:
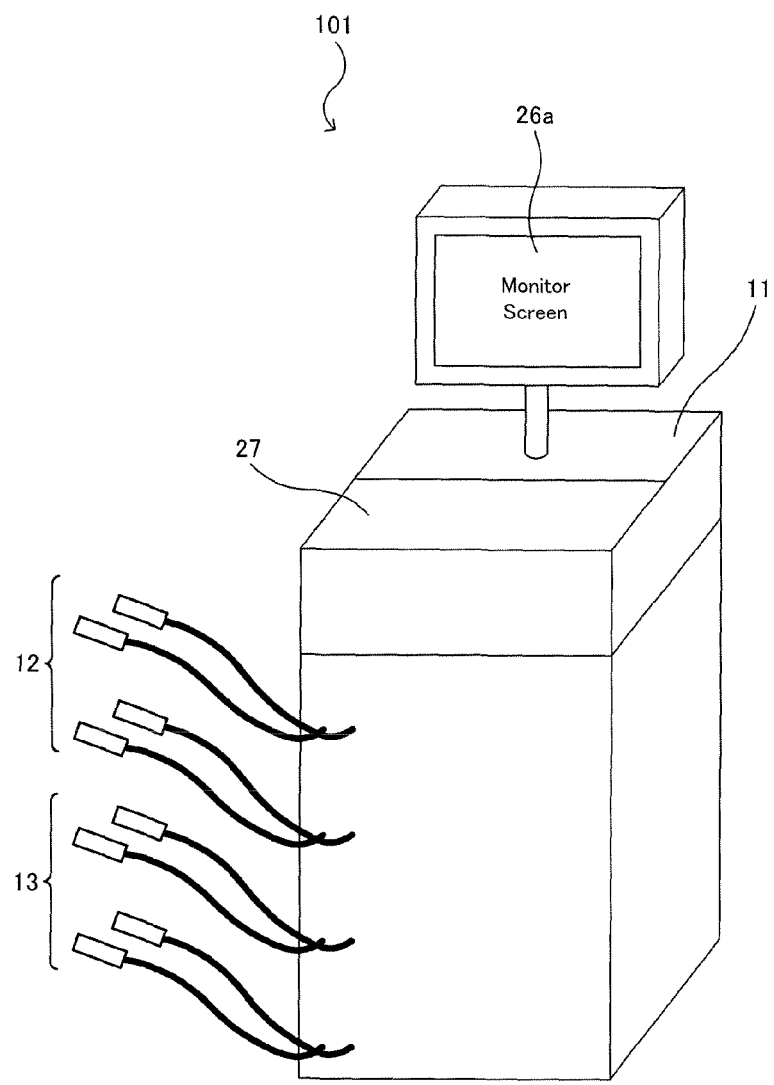
FIG. 14 is a perspective diagram showing the appearance of an example of the near-infrared spectrum analyzer in FIG. 13.
Figure 15:
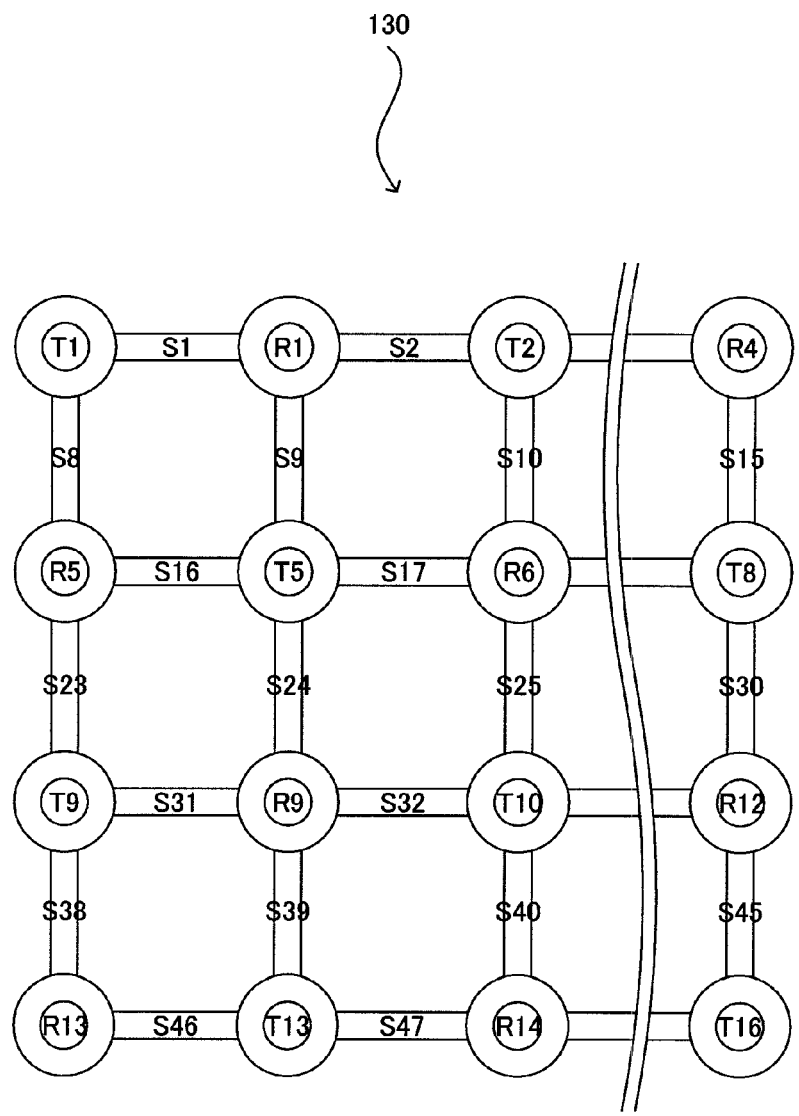
FIG. 15 is a plan diagram showing an example of the holder into which 16 light sending probes and 16 light receiving probes are inserted.

Next, in the optical measurement system 1, the examination method for measuring the chronological change in the blood flow through certain portions of the brain in the subject when the subject is exercising, such as for rehabilitation is described. FIG. 10 is a flow chart for illustrating an example of the examination method in the optical measurement system 1 in the case where the subject (patient) is rehabilitating mainly in a hospital.

First, in the process in step S201, the subject places the second holder 60 with the light sending probes $12_{T1}$ to $12_{T4}$ and the light receiving probes $13_{R1}$ to $13_{R4}$ on the surface of his or her own head. At this time, the subject alone can attach the second holder 60 with the light sending probes $12_{T1}$ to $12_{T4}$ and the light receiving probes $13_{R1}$ to $13_{R4}$ to his or her own head, and the preparation time for wearing the second holder 60 is very short (five minutes, for example).

Next, in the process in step S202, the subject inputs a start signal "rehabilitation" using the keyboard 27. That is to say, the main optical measurement device 10 is turned ON.

Next, in the process in step S203, the subject inputs a start signal by means of the switch 57 so that the control unit 51 for sending and receiving light outputs a drive signal to the light source driver 42, and at the same time, receives a light receiving signal from the light detector 43, and thus transmits a light receiving signal (information on the amount of received signal) $A(\lambda_1)$, $A(\lambda_2)$ and $A(\lambda_3)$ via the wireless device 46 (portable optical measurement device using step). At this time, the subject is exercising, such as for rehabilitation. In addition, the information on the amount of received light from ten places $A(\lambda_1)$, $A(\lambda_2)$ and $A(\lambda_3)$ is transmitted.

Next, in the process in step S204, the communication control unit 21c receives the information on the amount of received light $A(\lambda_1)$, $A(\lambda_2)$ and $A(\lambda_3)$ via the wireless device 6 and stores the information on the amount of received light $A(\lambda_1)$, $A(\lambda_2)$ and $A(\lambda_3)$ in the memory 23. That is to say, the information on the amount of received light $A(\lambda_1)$, $A(\lambda_2)$ and $A(\lambda_3)$ from the ten places is stored in the memory 23.

Next, in the process in step S205, the arithmetic operation unit 24b finds the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) from the intensity of light having the respective wavelengths that has passed through the optical path on the basis of the information on the amount of received light $A(\lambda_1)$, $A(\lambda_2)$ and $A(\lambda_3)$ that is being stored in the memory 23 using the simultaneous equations (1), (2) and (3).

Next, in the process in step S206, the brain activity image display control unit 24c displays the information on the monitor screen 26a. At this time, contour graphs are displayed on part of the brain.

Next, in the process in step S207, the doctor and the subject check the information displayed on the monitor screen 26a. At this time, the doctor can determine whether or not the course of measurement should be changed while the subject can check whether the rehabilitation is progressing well. That is to say, the subject can also check the procedure, which becomes an incentive for the rehabilitation.

Next, in the process in step S208, the subject removes the second holder 60 with the light sending probes $12_{T1}$ to $12_{T4}$ and the light receiving probes $13_{R1}$ to $13_{R4}$ from the surface of his or her own head.

Next, in the process in step S209, the doctor determines whether or not it is time for diagnosis on the basis of the course of measurement (determination step). When the doctor determines it is not the time for diagnosis, the procedure returns to the process in step S205. That is to say, the processes from step S201 to step S209 are to be repeated at the time of the next rehabilitation (next day, for example), and the processes from step S201 to step S209 can be carried out in a short preparation time. When it is determined to be a tune for diagnosis, in the process in step S210, the doctor or the like places the first holder 30 with the light sending probes $12_{T1}$ to $12_{R64}$ and the light receiving probes $13_{R1}$ to $13_{R64}$ on the surface of the head of the subject. At this time, it takes approximately one hour.

Next, in the process in step S211, the doctor or the like inputs a start signal "diagnosis" using the keyboard 27 so that the control unit 21 for sending and receiving light outputs a drive signal to the light source driver 2, and at the same time, receives a light receiving signal from the light detector 3, and thus stores the information on the amount of received light $A(\lambda_1)$, $A(\lambda_2)$ and $A(\lambda_3)$ in the memory 23 (main optical measurement device using step). That is to say the information on the amount of received light $A(\lambda_1)$, $A(\lambda_2)$ and $A(\lambda_3)$ from 232 portions is stored in the memory 23.

Next, in the process in step S212, the arithmetic operation unit 24b finds the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) from the intensity of light having the respective wavelengths that has passed through the optical path on the basis of the information on the amount of received light $A(\lambda_1)$, $A(\lambda_2)$ and $A(\lambda_3)$ that is being stored in the memory 23 using the simultaneous equations (1), (2) and (3).

Next, in the process in step S213, the brain activity image display control unit 24c displays the information on the monitor screen 26a. At this time, contour graphs are displayed on the entire surface of the brain.

Next, in the process in step S214, the doctor or the like determines whether he or she should have the subject continue with the rehabilitation or stop it while checking the information displayed on the monitor screen 26a (diagnosis step). At this time, the doctor can determine whether or not the course of measurement should be changed. As a result, when it is determined that the rehabilitation should still be continued, the procedure returns to the process in step S201. That is to say, the processes from step S201 to step S209 are repeated, but the processes from step S201 to step S209 can be carried out in a short preparation time.

When it is determined that the rehabilitation should be stopped, this flow chart is completed.

As described above, in the optical measurement system 1 according to the examples of the present invention, the portable optical measurement device 40 is provided with four light sending probes $12_{T1}$ to $12_{T4}$ and four light receiving probes $13_{R1}$ to $13_{R4}$, and it is not necessary for it to be provided with a display device, and therefore, size of the second case 41 can be made compact so that the subject can carry it, and as a result, measurement is possible even when the movement of the subject is very active.

In addition, the subject alone can attach the second holder 60 with the light sending probes $12_{T1}$ to $12_{T4}$ and the light receiving probes $13_{R1}$ to $13_{R4}$ to his or her own head, and the preparation time for wearing the second holder 20 is very short. Accordingly, the chronological change in the blood flow through some portions in the brain of the subject can be easily measured when the subject is exercising, such as for rehabilitation.

Furthermore, in the optical measurement system 1 according to examples of the present invention, only eight through holes are provided with the second holder 60, and the second holder 60 can be selected or fabricated so that the chronological change in the blood flow through certain portions in the brain of the subject can be measured without fail.

Figure 16:
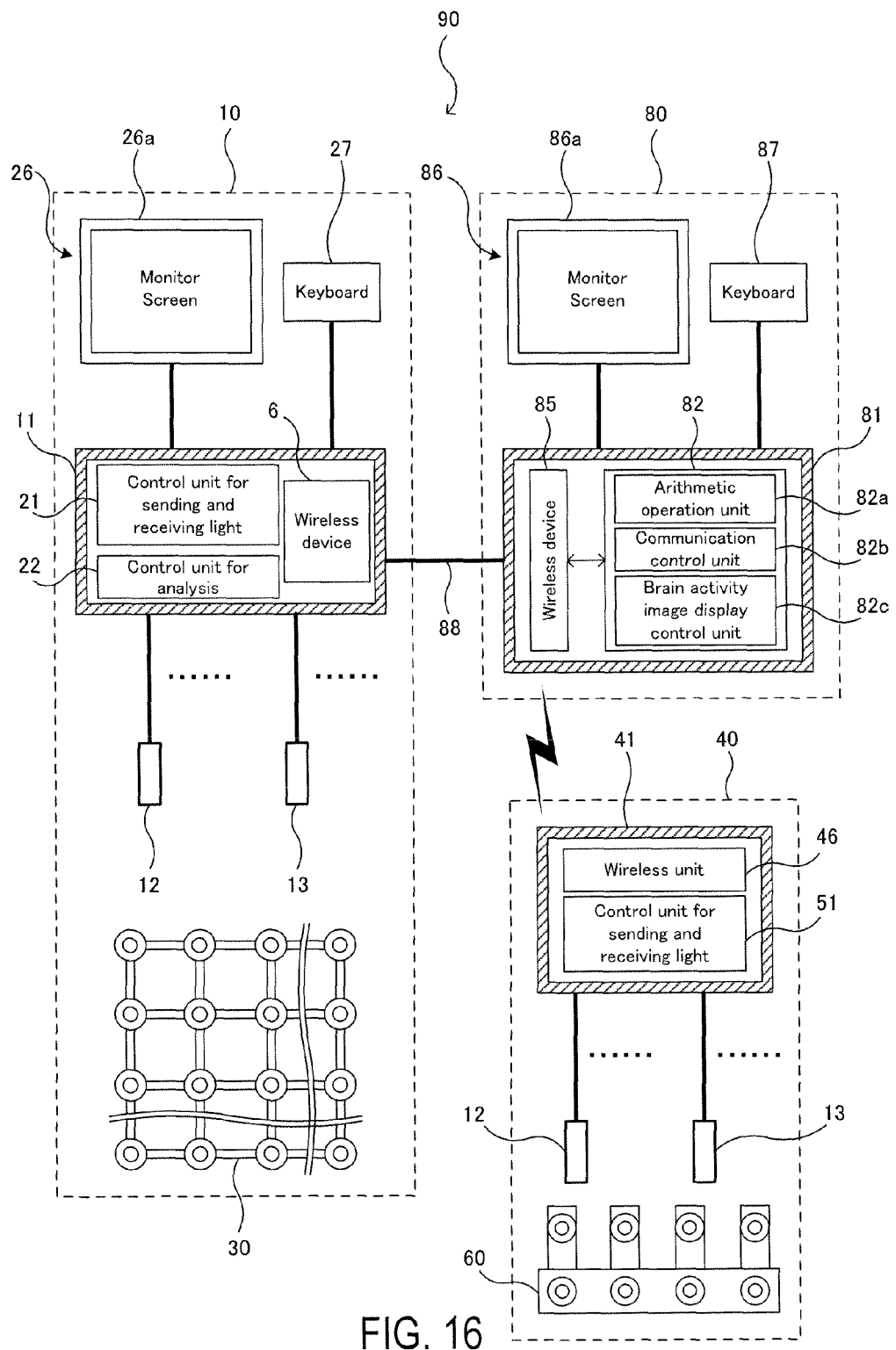
FIG. 16 is a block diagram schematically showing an example of the structure of the optical measurement system according to another embodiment of the present invention.

FIG. 16 is a block diagram schematically showing the structure of the optical measurement system according to another example of the present invention. The same symbols are attached to the same components as in the optical measurement system 1.

An optical measurement system 90 is provided with one main optical measurement device 10 having a first holder 30, one portable optical measurement device 40 having second holder 60, and one analysis device 80.

According to this example, the main optical measurement device 10 is installed in a hospital, while the portable optical measurement device 40 and the analysis device 80 are installed at the home of the subject. In addition, communication is possible between the main optical measurement device 10 and the analysis device 80 through the Internet 88 or the like.

The analysis device 80 has a third case 81 in rectangular parallelepiped form (50 cm×50 cm×50 cm, for example).

The inside of the third case 81 is provided with a wireless device (communication unit) 85 for wirelessly communicating with the control unit 51 for sending and receiving light of the portable optical measurement device 40, a control unit 82 for analysis and a memory 83, and at the same time, the outside of the third case 81 is provided with a display device 86 having a monitor screen 86a and the like and a keyboard (input device) 87.

The functions resulting from the process by the control unit 82 for analysis are described in the blocks in FIG. 16. The control unit 82 for analysis has an arithmetic operation unit 82a, a brain activity image display control unit 82c and a communication control unit 82b for controlling the wireless device 85.

Upon reception of a start signal "rehabilitation" from the keyboard 87, the communication control unit 82b controls the system so that the information on the amount of received light $A(\lambda_1)$, $A(\lambda_2)$ and $A(\lambda_3)$ obtained in the control unit 51 for sending and receiving light in the portable optical measurement device 40 is received via the wireless device 85 and stored in the memory 83.

The arithmetic operation unit 82a controls the system so that the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) are found from the intensity of light having the respective wavelengths (wavelength absorbed by oxyhemoglobin and wavelength absorbed by deoxyhemoglobin) that has passed through the optical path on the basis of the information on the amount of received light $A(\lambda_1)$, $A(\lambda_2)$ and $A(\lambda_3)$ that is being stored in the memory 83 using the simultaneous equations (1), (2) and (3).

The brain activity image display control unit 82c controls the system so that information is displayed on the monitor screen 86a. Contour graphs of the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) are displayed in planes of the brain, for example. At this time, contour graphs for part of the brain are displayed.

Figure 17:
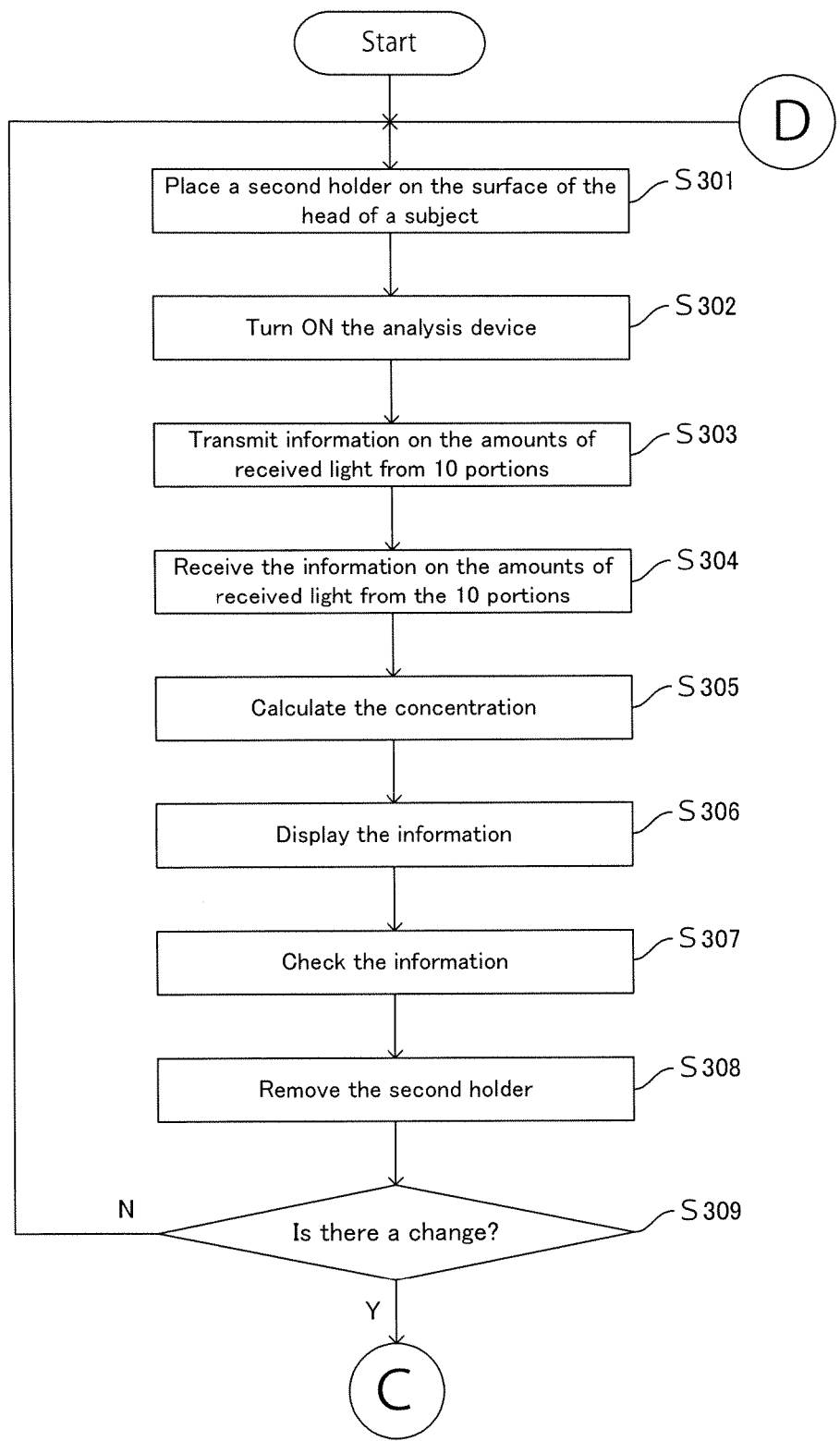
FIG. 17 is a flow chart for illustrating an example of the examination method in the optical measurement system.
Figure 18:
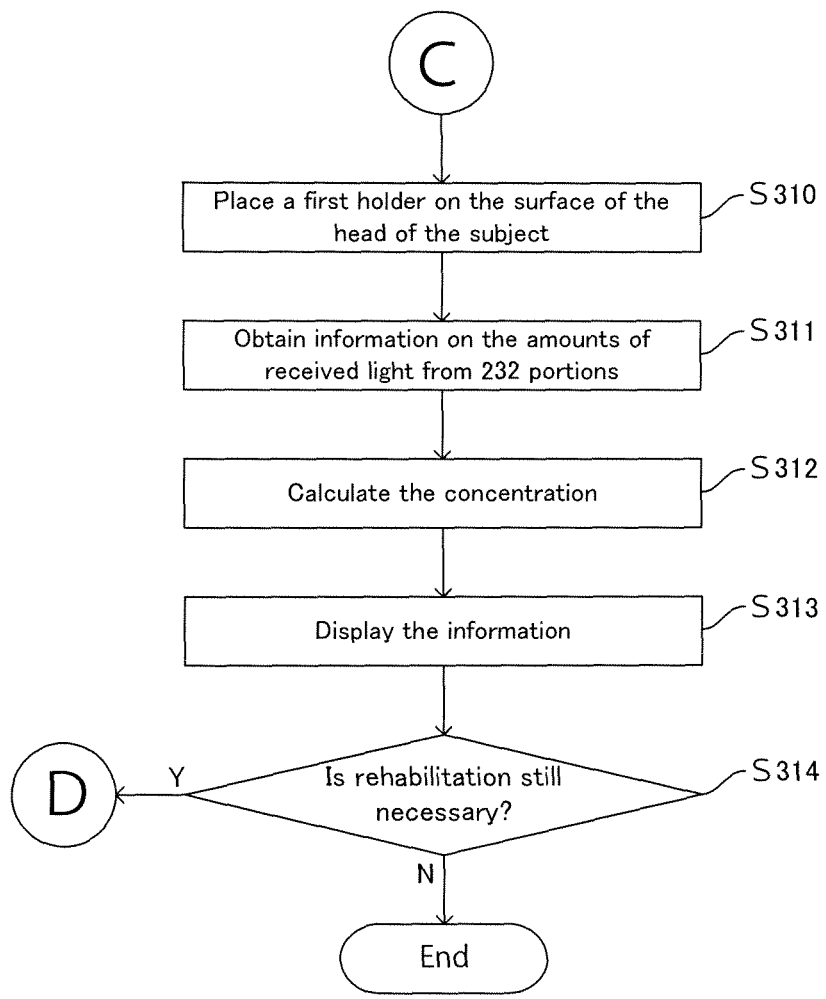
FIG. 18 is a flow chart for further illustrating the example of the examination method in the optical measurement system.

Next, in the case where the subject (patient) rehabilitates mainly out of the hospital, such as at home, the examination method for measuring the chronological change in the blood flow through some portions in the brain of the subject when the subject is exercising, such as for rehabilitation, is described. FIG. 17 is a flow chart for illustrating an example of the examination method in the optical measurement system 90.

First, in the process in step S301, the subject places the second holder 60 with the light sending probes $12_{T1}$ to $12_{T4}$ and the light receiving probes $13_{R1}$ to $13_{R4}$ on the surface of his or her own head. At this time, the subject alone can attach the second holder 60 with the light sending probes $12_{T1}$ to $12_{T4}$ and the light receiving probes $13_{R1}$ to $13_{R4}$ to his or her own head, and the preparation time for wearing the second holder 60 is very short (five minutes, for example).

Next, in the process in step S302, the subject inputs a start signal "rehabilitation" using the keyboard 87. That is to say, the analysis device 80 is turned ON.

Next, in the process in step S303, the subject inputs a start signal by means of the switch 57 so that the control unit 51 for sending and receiving light outputs a drive signal to the light source driver 42, and at the same time receives a light receiving signal from the light detector 43, and thus transmits the light receiving signal (information on the amount of received light) $A(\lambda_1)$, $A(\lambda_2)$ and $A(\lambda_3)$ via the wireless device 46 (portable optical measurement device using step). At this time, the subject is exercising, such as for rehabilitation. Thus, the information on the amount of received light $A(\lambda_1)$, $A(\lambda_2)$ and $A(\lambda_3)$ from ten portions is transmitted.

Next, in the process in step S304, the communication control unit 82b receives the information on the amount of received light $A(\lambda_1)$, $A(\lambda_2)$ and $A(\lambda_3)$ via the wireless device 85 and stores the information on the amount of received light $A(\lambda_1)$, $A(\lambda_2)$ and $A(\lambda_3)$ in the memory 83. That is to say, the information on the amount of received light $A(\lambda_1)$, $A(\lambda_2)$ and $A(\lambda_3)$ from ten portions is stored in the memory 83.

Next, in the process in step S305, the arithmetic operation unit 82a finds the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) from the intensity of light ha ring the respective wavelengths that has passed through the optical path on the basis of the information on the amount of received light $A(\lambda_1)$, $A(\lambda_2)$ and $A(\lambda_3)$ that is being stored in the memory 83 using the simultaneous equations (1), (2) and (3).

Next, in the process in step S306, the brain activity image display control unit 82c displays the information on the monitor screen 86a. At this time, contour graphs for part of the brain are displayed.

Next, in the process in step S307, the subject checks the information displayed on the monitor screen 86a. At this time, the subject can check whether the rehabilitation is progressing well. Here, communication is possible between the main optical measurement device 10 and the analysis device 80 through the Internet 88 or the like, and therefore, the subject may communicate with the doctor at the hospital so that the doctor can check the progress.

Next, in the process in step S308, the subject removes the second holder 60 with the light sending probes $12_{T1}$ to $12_{T4}$ and the receiving probes $13_{R1}$ to $13_{R4}$ from the surface of his or her own head.

Next, in the process in step S309, the subject determines whether or not the contour graphs for part of the brain have changed (determination step). When it is determined that there is no change, the procedure returns to the process in step S301. That is to say, the processes from step S301 to step S309 are repeated, and the processes from step S301 to step S309 can be carried out at the home of the subject and can be carried out by the subject alone in a short preparation time.

When it is determined that there has been a change, the subject goes to the hospital for the process in step S310 where the doctor or the like places the first holder 30 with the light sending probes $12_{T1}$ to $12_{T64}$ and the light receiving probes $13_{R1}$ to $13_{R64}$ on the surface of the head of the subject. At this time, it takes approximately one hour.

Next, in the process in step S311, the doctor or the like inputs a start signal "diagnosis" using the keyboard 27 so that the control unit 21 for sending and receiving light outputs a drive signal to the light source driver 2, and at the same time, receives a light receiving signal from the light detector 3, and thus stores the light receiving signal (information on the amount of received light) $A(\lambda_1)$, $A(\lambda_2)$ and $A(\lambda_3)$ in the memory 23 (main optical measurement device using step). That is to say, the information on the amount of received light $A(\lambda_1)$, $A(\lambda_2)$ and $A(\lambda_3)$ from 232 portions is stored in the memory 23.

Next, in the process in step S312, the arithmetic operation unit 24b finds the product of the concentration of oxyhemoglobin and the length of the optical path [oxyHb], the product of the concentration of deoxyhemoglobin and the length of the optical path [deoxyHb], and the product of the concentration of the total amount of hemoglobin and the length of the optical path ([oxyHb]+[deoxyHb]) from the intensity of light having the respective wavelengths that has passed through the optical path on the basis of the information on the amount of received light $A(\lambda_1)$, $A(\lambda_2)$ and $A(\lambda_3)$ that is being stored in the memory 23 using the simultaneous equations (1), (2) and (3).

Next, in the process in step S313, the brain activity image display control unit 24c displays the information on the monitor screen 26a. At this time, contour graphs are displayed on the entire surface of the brain.

Next, in the process in step S314, the doctor or the like determines whether he or she should have the subject continue with the rehabilitation or stop it while checking the information displayed on the monitor screen 26a (diagnosis step). At this time, the doctor can determine whether or not the course of measurement should be changed. As a result, when it is determined that the rehabilitation should still be continued, the procedure returns to the process in step S301. That is to say, the processes from step S301 to step S309 are repeated, but the processes from step S301 to step S309 can be carried out at the home of the subject and can be carried out by the subject alone in a short preparation time.

When it is determined that the rehabilitation should be stopped, this flow chart is completed.

As described above, in the optical measurement system 90 according to the example of the present invention, the portable optical measurement device 40 can be used only with the analysis device 80 even in places where there is no main optical measurement device 10. Accordingly, measurement is possible even in the case where the subject exercises, such as for rehabilitation, at home, for example.

Though in the above-described optical measurement system 1 the portable optical measurement device 40 has such a structure as to be provided with four light sending probes $12_{T1}$ to $12_{T4}$ and four light receiving probes $13_{R1}$ to $13_{R4}$, the structure may be provided with eight light sending probes and eight light receiving probes or eight light sending probes and four light receiving probes, for example. In addition, though the main optical measurement device 10 has such a structure as to be provided with 64 light sending probes $12_{T1}$ to $12_{T64}$ and 64 light receiving probes $13_{R4}$ to $13_{R64}$, the structure may be provided with 32 light sending probes and 32 light receiving probes or 32 light sending probes and 64 light receiving probes, for example.

Though in the above-described optical measurement system 1 the one main optical measurement device 10 has such a structure as to be able to communicate with one portable optical measurement device 40, the structure may be able to communicate with three portable optical measurement devices, for example.

Though in the above-described optical measurement system 1 the first holder 30 is used, another type of holder where 128 through holes are provided may be used.

Though in the above-described optical measurement system 1 the main optical measurement device 10 and the portable optical measurement device 40 have such a structure as to wirelessly communicate with each other using the wireless devices 6 and 46, the structure may make communication possible in such a manner that data is passed from the portable optical measurement device to the main optical measurement device using a portable memory, for example.

The present invention can be applied to an optical measurement system for obtaining information on the inside of a living thing by irradiating the inside of the living thing with light.

The invention claimed is:

1. An optical measurement system, comprising a main optical measurement device and a portable optical measurement device, wherein
said main optical measurement device comprises:
a first case;
Ath first light emitting probes configured to irradiate a subject with light, wherein A is a positive integer;
Bth first light receiving probes configured to receive the light from said subject, wherein B is a positive integer;
a first display device;
a first holder configured to be worn on a head of said subject, to which through holes are provided to support the first light emitting probes and the first light receiving probes, the first holder being configured to arrange the first light receiving probes to receive the light through a brain of the subject from the respective first light emitting probes for measuring brain activity of the subject; and
a first controller, provided inside said first case, for controlling said first light emitting probes and said first light receiving probes so as to obtain measurement data on the brain activity of the subject and display the measurement data on the first display device, and
said portable optical measurement device comprises:
a second case that is portable by the subject;
Cth second light emitting probes configured to irradiate the subject with light, wherein C is a positive integer;
Dth second light receiving probes configured to receive light from said subject, wherein D is a positive integer;
a second holder configured to be worn on the head of said subject, to which through holes are provided to support the second light emitting probes and the second light receiving probes, the second holder being configured to arrange the second light receiving probes to receive the light through the brain of the subject from the respective second light emitting probes for measuring brain activity of the subject;
a second controller, provided inside said second case, for controlling the second light emitting probes and the second light receiving probes so as to obtain measurement data on the brain activity of the subject; and
a communication device configured to communicate with said main optical measurement device, the communication device being one of a wireless communication device or a wired communication device, wherein (C+D)<(A+B) is satisfied, and
the communication device of said portable optical measurement device transmits the measurement data obtained by the second controller of said portable optical measurement device to the main optical measurement device.

2. The optical measurement system according to claim 1, wherein the second holder used in said portable optical measurement device is selected or fabricated on the basis of the measurement data obtained by the control unit of said main optical measurement device.

3. The optical measurement system according to claim 1, wherein
the measurement data obtained by the second controller of said portable optical measurement device is data when said subject is exercising, and
the measurement data obtained by the second controller of said main optical measurement device is data when said subject is at rest.

4. The optical measurement system according to claim 1, further comprising an analysis device including a second display device and a third controller configured to display on the second display device the measurement data from the portable optical measurement device, wherein
the communication device of said portable optical measurement device transmits the measurement data obtained by the second controller of said portable optical measurement device to the analysis device.

5. A rehabilitation planning method using the optical measurement system according to claim 1, the method comprising:
obtaining measurement data by the portable optical measurement device when the subject is exercising;
sending the measurement data from the portable optical measurement device to the main optical measurement device;
diagnosing the subject by showing the measurement data from the portable optical measurement device on the first display device of the main optical measurement device;
determining whether obtaining measurement data by the main optical measurement device is required;
if required, obtaining measurement data by the main optical measurement device when the subject is at rest; and
diagnosing the subject by showing the measurement data from the main optical measurement device on the first display device.

6. A portable optical measurement device used with a main optical measurement device, the main optical measurement device comprising: Ath first light emitting probes configured to irradiate a subject with light, wherein A is a positive integer; Bth first light receiving probes configured to receive light from the subject, wherein B is a positive integer; a display device; a first holder configured to be worn on a head of the subject, to which through holes are provided to support the first light emitting probes and the first light receiving probes, the first holder being configured to arrange the first light receiving probes to receive the light through a brain of the subject from the respective first light emitting probes for measuring brain activity of the subject; and a first controller configured to control the first light emitting probes and the first light receiving probes so as to obtain measurement data on brain activity of the subject and display the measurement data on the display device,
the portable optical measurement device comprising:
Cth second light emitting probes configured to irradiate the subject with light, wherein C is a positive integer;
Dth second light receiving probes configured to receive light from the subject, wherein D is a positive integer;
a second holder configured to be worn on the head of the subject, to which through holes are provided to support the second light emitting probes and the second light receiving probes, the second holder being configured to arrange the second light receiving probes to receive the light through the brain of the subject from the respective second light emitting probes for measuring brain activity of the subject;

a second controller configured to control the second light emitting probes and the second light receiving probes so as to obtain measurement data on brain activity of the subject; and a communication device configured to communicate with the main optical measurement device, the communication device being one of a wireless communication device or a wired communication device, wherein $(C+D)<(A+B)$ is satisfied, and the communication device of the portable optical measurement device transmits the measurement data obtained by the second controller of the portable optical measurement device to the main optical measurement device.

7. The portable optical measurement device according to claim 6, wherein said communication device transmits to the main optical measurement device the measurement data when said subject is exercising.

* * * * *